(12) United States Patent
Arora et al.

(10) Patent No.: US 7,691,837 B2
(45) Date of Patent: Apr. 6, 2010

(54) PYRROLE DERIVATIVES AS ANTIMYCOBACTERIAL COMPOUNDS

(75) Inventors: Sudershan Kumar Arora, Pune (IN); Neelima Sinha, Pune (IN); Sanjay Jain, Pune (IN); Ram Shankar Upadhayaya, Pune (IN); Gourhari Jana, Pune (IN); Shankar Ajay, Pune (IN); Rakesh Kumar Sinha, Pune (IN)

(73) Assignee: Lupin Limited, Mumbai (IN)

( * ) Notice: Subject to any disclaimer, the term of this patent is extended or adjusted under 35 U.S.C. 154(b) by 710 days.

(21) Appl. No.: 10/497,615

(22) PCT Filed: Sep. 20, 2002

(86) PCT No.: PCT/IN02/00189

§ 371 (c)(1),
(2), (4) Date: Dec. 20, 2004

(87) PCT Pub. No.: WO2004/026828

PCT Pub. Date: Apr. 1, 2004

(65) Prior Publication Data

US 2005/0107370 A1    May 19, 2005

(51) Int. Cl.
| | |
|---|---|
| *A01N 43/00* | (2006.01) |
| *A01N 43/40* | (2006.01) |
| *A61K 31/33* | (2006.01) |
| *A61K 31/55* | (2006.01) |
| *A61K 31/497* | (2006.01) |
| *A61K 31/435* | (2006.01) |
| *C07D 223/00* | (2006.01) |
| *C07D 243/00* | (2006.01) |
| *C07D 241/04* | (2006.01) |
| *C07D 295/00* | (2006.01) |
| *C07D 213/00* | (2006.01) |

(52) U.S. Cl. ............. 514/183; 514/212.01; 514/252.12; 514/277; 540/484; 540/553; 544/358; 546/1

(58) Field of Classification Search ....................... None
See application file for complete search history.

(56) References Cited

U.S. PATENT DOCUMENTS

| 2,986,564 A | 5/1961 | Rips |
| 3,168,531 A | 2/1965 | Short |
| 3,168,532 A | 2/1965 | Short |
| 3,246,010 A | 4/1966 | Creger |

FOREIGN PATENT DOCUMENTS

DE    1 938 904    2/1970

OTHER PUBLICATIONS

Calloway. Chemical Reviews, 1935, 17(3), 327-92.*
Biava et al. "New Pyrrole Derivatives as Antimycobacterial Agents Analogs of BM212" Bioorganic & Medicinal Chemistry Letters 9 (1999) p. 2983-2988.

Cerreto et al. "Studies on Anti-Candida Agents with Pyrrole Moiety. Synthesis and Microbiological Activity of some 3-aminomethyl-1,5-diaryl-2-methyl-pyrrole derivatives" European Journal of Medicinal Chemistry vol. 27 (1992) p. 701-708.

Porretta et al. "Research on Antibacterial and Antifungal Agents. XII—Synthesis and Antimicrobial Activity of some Mannich Bases of Diarylpyrroles" II Farmaco, Societa Chimica Italiana 50 (9) (1995) p. 617-623.

Cerreto et al. "Synthesis and Antimicrobial Activity of some 1,5-diaryl-2-methyl-3-carbethoxy-4-(4-methyl-piperazin-l-ylmethyl)-pyrroles and some 1,5-diaryl-2-methyl-3,4-di(4-methyl-piperazin-l-ylmethyl)-pyrroles" II Farmaco, 48 (12), (1993) p. 1735-1746.

Biava et al. "Synthesis and Microbiological Activities of Pyrrole Analogs of BM 212, a potent antitubercular Agent" Medicinal Chemistry Research 9:1 (1999) p. 19-34.

Porretta et al. "Research on Antibacterial and Antifungal Agents IX Synthesis and Microbiological Activity of new N-Arylpyrroles" II Farmaco, 46 (7,8), (1991) p. 987-995.

Biava et al. "Study of the Mannich Reaction: β-Amino-Methylation of N-Aryl and N-Azaheteroaryl-Substituted 2, 5-Dimethylpyrroles, Compounds with Potential Biological Activity" II Farmaco, 50 (6) (1995) p. 431-438.

Scalzo et al. "Studies on Anti-Candida Agents with a Pyrrole Moiety. Synthesis and Microbiological activity of some [(1-Alkyl), (1-Aryl) and (1-Benzyl)-5-Aryl-3-Carboxamido-2-Methyl] Pyrrole Derivatives." II Farmaco 47 (7,8), (1992) p. 1047-1053.

Roy et al., "Recent advance in research on antituberculars," *J. Indian Chem. Soc* (2002) 79: 320-335.

(Continued)

*Primary Examiner*—James O Wilson
*Assistant Examiner*—Noble Jarrell
(74) *Attorney, Agent, or Firm*—Merchant & Gould P.C.

(57) ABSTRACT

Novel pyrrole derivatives of formula (I)

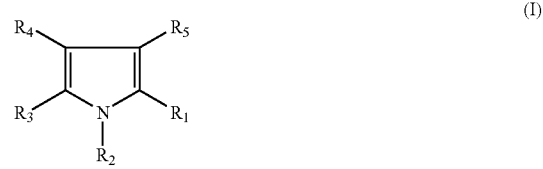

and their pharmaceutically acceptable acid addition salts having superior antimycobacterial activity against clinically sensitive as well as resistant strains of *Mycobacterium tuberculosis* as well as having lesser toxicity compared to known compounds. The use of the novel compounds of formula (I) for treatment of latent tuberculosis including Multi Drug Resistant Tuberculosis (MDR TB). The methods for preparation of the novel compounds, pharmaceutical compositions containing the novel compounds and method of treating MDR TB by administration of compounds of formula (I).

22 Claims, No Drawings

OTHER PUBLICATIONS

Ragno et al., "Antimycobacterial Pyrroles: Synthesis, Anti-*Mycobacterium tuberculosis* Activity and QSAR Studies," *Bioorganic & Medicinal Chemistry* (2000) 8: 1423-1432.

Gillet et al., "Pyrroleacetic acid derivatives in anti-inflammatory and analgesic activity," *Eur. J. Med. Chem. Chim. Ther.* (1976) 11 (2): 173-181.

Deidda et al., "Bactericidal activities of the pyrrole derivative BM212 against multidrug-resistant and intramacrophagic *Mycobacterium tuberculosis* strains," *Antimicrobial Agents and Chemotherapy* (1998) 42 (11): 3035-3037.

Buu-Hoi et al., "1,2,5-Trisubstituted pyrroles of pharmacologic interest," *J. Org. Chem.* (1960) 25 (3): 390-392.

Ragno et al., "Antimycobacterial Pyrroles: Synthesis, Anti-*Mycobacterium tuberculosis* Activity and QSAR Studies," *Bioorganic & Medicinal Chemistry* (2000) 8: 1423-1432.

Office Action for co-pending U.S. Appl. No. 12/137170 mailed on May 14, 2009.

Wijngaarden et al., "2-Phenylpyrroles as conformationally restricted benzamide analogues. A new class of potential antipsychotics," *J. Med. Chem.* (1988) 31: 1934-1940.

* cited by examiner

PYRROLE DERIVATIVES AS ANTIMYCOBACTERIAL COMPOUNDS

FIELD OF THE INVENTION

The present invention relates to novel 3- and/or 4-(4-substituted-piperazinyl)alkyl pyrroles of Formula (I),

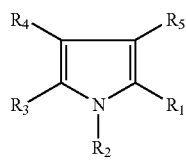

(I)

and their pharmaceutically acceptable acid addition salts thereof, possessing excellent antimycobacterial activity against clinically sensitive as well as resistant strains of *Mycobacterium tuberculosis*. The antimycobacterial activity of the compounds of the present invention are found to be superior to those of previously known compounds. The present invention also relates to use of the novel compounds for treatment of latent tuberculosis including Multi Drug Resistant Tuberculosis (MDR TB). The invention further relates to methods for preparation of the novel compounds and pharmaceutical compositions containing the said novel compounds.

BACKGROUND OF THE INVENTION

Tuberculosis (TB) is a contagious disease, which usually runs a protracted course, ending in death in majority of the cases, with relapse being a common feature of the disease. It is one of the most important causes of prolonged disability and chronic ill health. It is caused by the tubercle *bacillus Mycobacterium tuberculosis*, which is comparatively difficult to control. Drugs such as isoniazid, rifampicin, pyrazinamide, ethambutol streptomycin, para-aminosalisylic acid, ethionamide, cycloserine, capreomycin, kanamycin, thioacetazone etc. have been and are being currently used to treat TB. Amongst these, isoniazid, rifampicin, ethambutol and pyrazinamide are the first-line drugs of choice, which are administrated either as a single drug formulation or as a fixed-dose combination of two or more of the aforesaid drugs.

Even though, each of the abovementioned first-line drug regimen is highly effective for treatment of TB, however, they are associated with shortcomings, such as unpleasant side-effects and relatively long course of treatment. The later one results in non-compliance of the patient to the treatment leading often to failure of the treatment and most importantly, development of drug resistance. The development of drug resistance has long constituted a principal difficulty in treating human tuberculosis. The second-line drugs, on the other hand are less effective, more expensive and more toxic.

It is estimated that in the next twenty years over one billion people would be newly infected with TB, with 35 million people succumbing to the disease (WHO Fact Sheet No. 104, Global Alliance for TB Drug Development—Executive Summary of the Scientific Blueprint for TB Development: http://www.who.int/inf-fs/en/fact104.html). With the emergence of HIV related TB, the disease is assuming alarming proportions as one of the killer diseases in the world today.

A major thrust in research on antimycobacterials in the last decade has witnessed the development of new compounds for treatment of the disease, a) differing widely in structures, b) having different mode/mechanism of action, c) possessing favourable pharmacokinetic properties, d) which are safe and having low incidence of side-effects, and e) which provide a cost-effective dosage regimen.

Several new class of compounds have been synthesized and tested for activity against *Mycobacterium tuberculosis*, the details of chemistry and biology of which could be found in a recent review by B. N. Roy et. al. in *J. Ind. Chem. Soc.*, April 2002, 79, 320-335 and the references cited therein.

Substituted pyrrole derivatives constitute another class of compounds, which hold promise as antimycobacterial agents. The pyrrole derivatives which have been synthesized and tested for antitubercular as well as non-tubercular activity has been disclosed by:

a) D. Deidda et. al. in *Antimicrob. Agents and Chemother.*, November 1998, 3035-3037. This article describes the inhibitory activity shown by one pyrrole compound, viz. BM 212 having the structure shown below, against both *Mycobacterium tuberculosis* including drug-resistant mycobacteria and some non-tuberculosis mycobacteria.

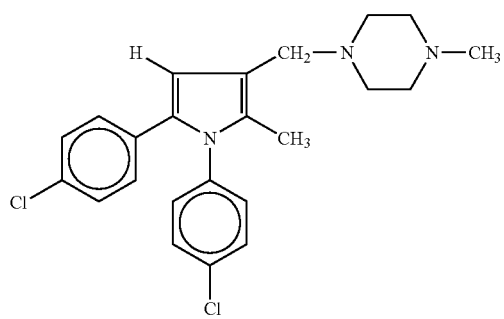

BM 212

The MIC value (µg/ml) against the *M. tuberculosis* strain 103471 exhibited by BM 212 was 0.70 as against 0.25 found for isoniazid.

b) M. Biava et. al. in *J. Med. Chem. Res.*, 1999, 19-34 have reported the synthesis of several analogues of BM 212, having the general formula (The compounds disclosed by M. Biava et. al. in *J. Med. Chem. Res.*, 1999, 19-34.) shown hereunder

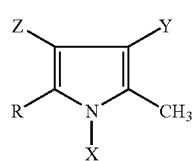

-continued wherein,

R is CH₃ or 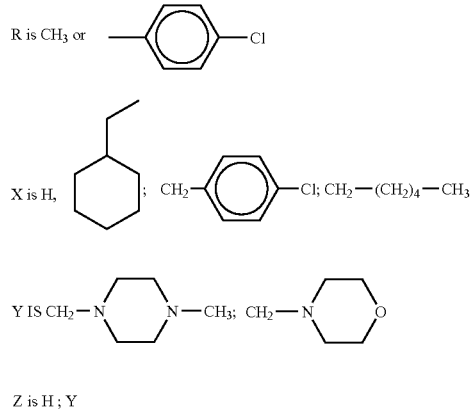

X is H,

Y IS CH₂—

Z is H ; Y and the in vitro antimicrobial activity of the compounds against *Candida albicans, Candida* sp, *Cryptococcus neoformans*, Gram-positive or Gram-negative bacteria, isolates of pathogenic plant fungi, Herpes simplex virus, both HSV1 and HSV2, *M. tuberculosis, M. smegmatis, M. marinum* and *M. avium*.

However, the MIC values (μg/ml) of these compounds against the *M. tuberculosis* strain 103471 are found to be inferior to BM 212 and are in the range of 4-16.

c) M. Biava et. al. *Bioorg. & Med. Chem. Lett.*, 1999, 9, 2983-2988. This article describes the synthesis of pyrrole compounds of formula (The compounds disclosed by M. Biava et. al. in *Bioorg. & Med. Chem. Lett.*, 1999, 9, 2983-2988) shown hereunder wherein,
X is H or Cl
Y is H or Cl
R is N-methyl piperazinyl or thiomorphinyl and their respective in vitro activity against *M. tuberculosis* and non-tuberculosis species of mycobacteria.

However, the MIC values (μg/ml) of these compounds against the *M. tuberculosis* strain 103471 are found to be inferior to BM 212 and are in the range of 2-4.

d) F. Cerreto et. al. in *Eur. J. Med. Chem.*, 1992, 27, 701-708 have reported the synthesis of certain 3-amino-1,5-diaryl-2-methylpyrrole derivatives and their in vitro anti-fungal activity against *Candida albicans* and *Candida* sp. However, there is no report on the activity of such compounds against *M. tuberculosis*.

e) C. Gillet et. al. in *Eur. J. Med. Chem.-Chimica Therapeutica*, March-April 1976, 11(2), 173-181 report the synthesis of several pyrrole derivatives useful as anti-inflammatory agents and as anti-allergants.

f) R. Ragno et. al., *Bioorg. & Med. Chem.*, 2000, 8, 1423-1432. This article reports the synthesis and biological activity of several pyrrole derivatives as well as describes a structure activity relationship between the said pyrrole compounds and antimycobacterial activity. The compounds (The compounds disclosed by R. Rango et. al., *Bioorg. & Med. Chem.*, 2000, 8, 1423-1432) synthesized and tested by the authors is summarized hereunder

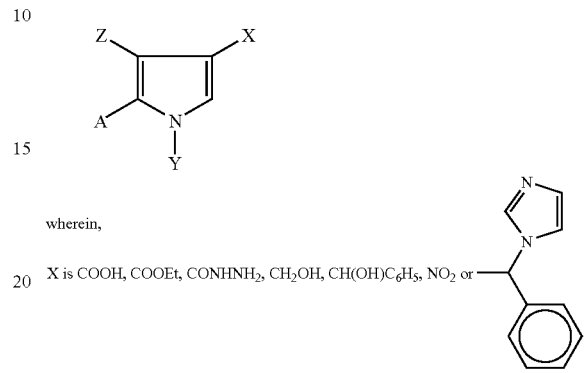

wherein,

X is COOH, COOEt, CONHNH₂, CH₂OH, CH(OH)C₆H₅, NO₂ or

Y is H, CH₃, OCH₃, CH₂, SO₂, or a group of formula

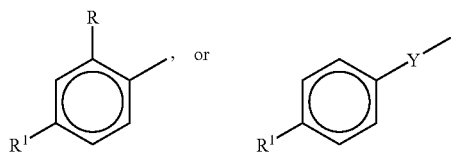

wherein,
R is H, Cl, C₂H₅, or OCH₃ and R¹ is H, Cl, F, CH₃, or NO₂,
A is H or R
Z is a group of formula,

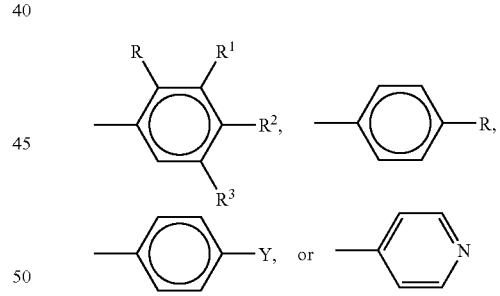

R² is H, Cl, OH, or OCH₃ and R³ is H or Cl

None of the abovementioned disclosures report or suggest the in vivo efficacy including toxicity of any of the compounds described therein against experimental tuberculosis in animal model. Moreover, the higher MIC values of the compounds reported suggest that they may not be very effective in inhibition of *Mycobacterium tuberculosis*.

OBJECTS OF THE INVENTION

It is thus the basic object of the present invention to meet the urgent demand, that exists for new antimycobacterial compounds by providing novel pyrrole derivatives which, a) exhibit significantly greater antimycobacterial activity, than existing drugs, b) provide safe and specific treatment of Multi Drug Resistant tuberculosis (MDR TB), and c) are useful in treatment of patients who harbour quiescent/latent tuberculosis.

SUMMARY OF THE INVENTION

In one aspect, the present invention provides a compound of formula (I) its tautomers, enantiomers, diastereomers, N-oxides, polymorphs and pharmaceutically acceptable salts thereof

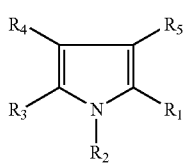

(I)

wherein, $R_1$ is a) $C_1$-$C_4$ alkyl, or b) $C_1$-$C_4$ alkoxy, or c) $C_1$-$C_4$ thioalkoxy, or d) trifluoroalkyl, or e) trifluoroalkoxy, or f) hydroxyalkyl $R_2$ is selected from a group consisting of i) phenyl which is unsubstituted or substituted with 1 or 2 substituents, each independently selected from the group consisting of halogen, $C_1$-$C_4$ alkyl, $C_1$-$C_4$ alkoxy, $C_1$-$C_4$ thioalkoxy, nitro, haloalkyl, haloalkoxy, unsubstituted or substituted piperazine, morpholine, thiomorpholine, pyrrolidine, and piperidine, or ii) hydroxyalkyl, or iii) unsubstituted or substituted thiazole, or iv) unsubstituted or substituted thiadiazole, or v) unsubstituted or substituted pyridine, or vi) unsubstituted or substituted naphthalene, or vii) NHCOR$_6$ wherein R$_6$ is aryl, unsubstituted or substituted heteroaryl, unsubstituted or substituted heterocyclyl.

$R_3$ is a) phenyl or substituted phenyl, or b) aryl, or c) unsubstituted or substituted heteroaryl.

when one of $R_4$ and $R_5$ is H, the other is —(CH$_2$)$_n$—R$_7$ wherein n=1-3 and $R_7$ is selected from the groups

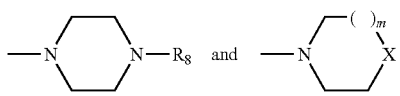

wherein $R_8$ is phenyl which is unsubstituted or substituted with 1-2 substituents each independently selected from the group consisting of halogen, $C_1$-$C_4$ alkyl, $C_1$-$C_4$ alkoxy, $C_1$-$C_4$ thioalkoxy, nitro, amino, haloalkyl, haloalkoxy etc.; unsubstituted or substituted benzyl; unsubstituted or substituted heteroaryl; unsubstituted or substituted heteroaroyl; unsubstituted or substituted diphenylmethyl, m=0-2 and X=NCH$_3$, CH$_2$, S, SO, or SO$_2$;

such that when $R_2$ is phenyl, which is unsubstituted or substituted with 1 or 2 substituents, each independently selected from the group consisting of halogen, $C_1$-$C_4$ alkyl, $C_1$-$C_4$ alkoxy, $C_1$-$C_4$ thioalkoxy, nitro, haloalkyl, haloalkoxy, unsubstituted or substituted piperazine, morpholine, thiomorpholine, pyrrolidine, and piperidine and $R_4$ is hydrogen; $R_8$ is not $C_1$-$C_4$ alkyl, or X is not —NCH$_3$, S, SO, or SO$_2$, when m=1, or X is not —CH$_2$, when m=0.

The above disclosed compound of formula (I), and its various forms including its pharmaceutically acceptable salts are safe and exhibit significantly low toxicity.

Another aspect of the present invention provides methods for synthesis of compound of formula (I) its tautomers, enantiomers, diastereomers, N-oxides, polymorphs and pharmaceutically acceptable salts thereof comprising:

reacting a compound of formula (V)

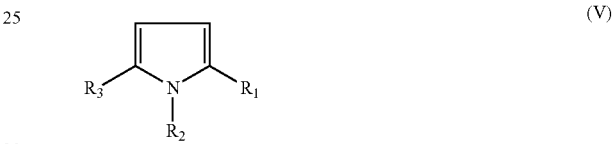

(V)

wherein $R_1$ is $C_1$-$C_4$ alkyl, $C_1$-$C_4$ alkoxy, $C_1$-$C_4$ thioalkoxy, trifluoroalkyl, trifluoroalkoxy or, hydroxyalkyl, $R_2$ is selected from a group consisting of i) phenyl which is unsubstituted or substituted with 1 or 2 substituents, each independently selected from the group consisting of halogen, $C_1$-$C_4$ alkyl, $C_1$-$C_4$ alkoxy, $C_1$-$C_4$ thioalkoxy, nitro, haloalkyl, haloalkoxy, unsubstituted or substituted piperazine, morpholine, thiomorpholine, pyrrolidine, and piperidine, or ii) hydroxyalkyl, or iii) unsubstituted or substituted thiazole, or iv) unsubstituted or substituted thiadiazole, or v) unsubstituted or substituted pyridine, or vi) unsubstituted or substituted naphthalene, or vii) NHCOR$_6$ wherein R$_6$ is aryl, unsubstituted or substituted heteroaryl, unsubstituted or substituted heterocyclyl.

$R_3$ is a) phenyl or substituted phenyl, or b) aryl, or c) unsubstituted or substituted heteroaryl.

with an amine of formula R$_7$H, wherein R$_7$ is selected from the groups

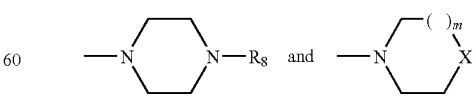

wherein $R_8$ is phenyl which is unsubstituted or substituted with 1-2 substituents each independently selected from the group consisting of halogen, $C_1$-$C_4$ alkyl, $C_1$-$C_4$ alkoxy, $C_1$-$C_4$ thioalkoxy, nitro, amino, haloalkyl, haloalkoxy etc.;

unsubstituted or substituted benzyl; unsubstituted or substituted heteroaryl; unsubstituted or substituted heteroaroyl; unsubstituted or substituted diphenylmethyl, m=0-2 and X=—NCH$_3$, CH$_2$, S, SO, or SO$_2$ such that in the compound of formula I thus produced when one of R$_4$ and R$_5$ is H, the other is —(CH$_2$)$_n$—R$_7$ wherein n=1-3 and R$_7$ is selected from the groups

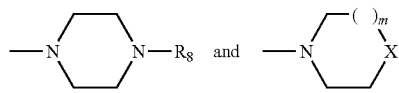

wherein R$_8$ is phenyl which is unsubstituted or substituted with 1-2 substituents each independently selected from the group consisting of halogen, C$_1$-C$_4$ alkyl, C$_1$-C$_4$ alkoxy, C$_1$-C$_4$ thioalkoxy, nitro, amino, haloalkyl, haloalkoxy etc.; unsubstituted or substituted benzyl; unsubstituted or substituted heteroaryl; unsubstituted or substituted heteroaroyl; unsubstituted or substituted diphenylmethyl, m=0-2 and X=—NCH$_3$, CH$_2$, S, SO, or SO$_2$;

such that when R$_2$ is phenyl, which is unsubstituted or substituted with 1 or 2 substituents, each independently selected from the group consisting of halogen, C$_1$-C$_4$ alkyl, C$_1$-C$_4$ alkoxy, C$_1$-C$_4$ thioalkoxy, nitro, haloalkyl, haloalkoxy, unsubstituted or substituted piperazine, morpholine, thiomorpholine, pyrrolidine, and piperidine and R$_4$ is hydrogen; R$_8$ is not C$_1$-C$_4$ alkyl, or X is not —NCH$_3$, S, SO, or SO$_2$, when m=1, or X is not —CH$_2$, when m=0.

It yet another further aspect the present inventions provides pharmaceutical compositions useful in the treatment of mycobacterial conditions such as tuberculosis including Multi Drug Resistant Tuberculosis (MDR TB) comprising a) at least one of compound of formula (I), its tautomers, enantiomers, diastereomers, N-oxides, polymorphs and pharmaceutically acceptable salts thereof and b) pharmaceutically acceptable additives.

In yet another aspect, the present invention provides a method of inhibiting/treating the microbial cell/conditions with a compound selected from compound of formula (I), its tautomers, enantiomers, diastereomers, N-oxides, polymorphs, its pharmaceutically acceptable salts with or without pharmaceutically acceptable carriers. The microbial cell/condition can be of *Mycobacterium tuberculosis*, drug resistant *Mycobacterium tuberculosis*, *Mycobacterium avium-intracellulare* complex, *Mycobacterium fortuitum* or *Mycobacterium kansasii*.

DETAILED DESCRIPTION OF THE INVENTION

In the pharmaceutically active compound of formula (I) of this invention,

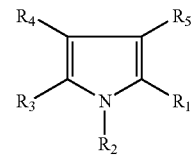

the definition of the groups R$_1$, R$_2$, R$_3$, R$_4$, and R$_5$ are as follows R$_1$ is a) C$_1$-C$_4$ alkyl, both straight and branched, or b) C$_1$-C$_4$ alkoxy, or c) C$_1$-C$_4$ thioalkoxy, or d) trifluoroalkyl, or e) trifluoroalkoxy, or f) hydroxyalkyl Suitable alkyl groups are methyl, ethyl, n-propyl, n-butyl, iso-propyl, iso-butyl, or tert-butyl. Methyl is preferred.

Suitable alkoxy groups are methoxy, ethoxy, n-propoxy, iso-propoxy, n-butoxy, iso-propopxy, iso-butoxy, and tert-butoxy.

Suitable thioalkyl groups are thiomethyl, thioethyl, 1-propanethio, 2-propanethio, 1-butanethio, 1-methyl-1-propanethio, and 1-methyl-2-propanethio.

Suitable trifluoroalkyl groups are trifluoromethyl, and trifluoroethyl.

Suitable trifluoroalkoxy groups are trifluoromethoxy, and trifluoroethoxy.

Suitable hydroxyalkyl groups are selected from trifluoromethoxy and trifluoroethoxy, R$_2$ is selected from a group consisting of:

i) phenyl which is unsubstituted or substituted with 1 or 2 substituents, each independently selected from the group consisting of halogen, C$_1$-C$_4$ alkyl, C$_1$-C$_4$ alkoxy, C$_1$-C$_4$ thioalkoxy, nitro, haloalkyl, haloalkoxy, unsubstituted or substituted piperazine, morpholine, thiomorpholine, pyrrolidine, and piperidine, or ii) hydroxyalkyl, or iii) unsubstituted or substituted thiazole, or iv) unsubstituted or substituted thiadiazole, or v) unsubstituted or substituted pyridine, or vi) unsubstituted or substituted naphthalene, or vii) NHCOR$_6$ wherein R$_6$ is aryl, unsubstituted or substituted heteroaryl, unsubstituted or substituted heterocyclyl.

The substituted phenyl groups are selected from but not limited to chlorobenzene, bromobenzene, fluorobenzene, 1,2-dichlorobenzene, 1,2-dibromobenzene, 1,2-difluorobenzene, 1,3-dichlorobenzene, 1,3-dibromobenzene, 1,3-difluorobenzene, 1,4-difluorobenzene, 1,4-dibromobenzene, 1,4-difluorobenzene, methylbenzene, ethylbenzene, o-xylene, m-xylene, p-xylene, 2-ethyl toluene, 3-ethyl toluene, 4-ethyl toluene, propyl benzene, cumene, butyl benzene, sec-butyl benzene, iso-butyl benzene, tert-butyl benzene, o-cymene, m-cymene, p-cymene, 1,2-diethyl benzene, 1,3-diethyl benzene, 1,4-diethylbenzene, 1,3-di-tert-butyl benzene, 1,4-di-tert-butyl benzene, 4-tert butyl toluene, anisole, 2-methyl anisole, 3-methyl anisole, 4-methyl anisole, 1,2-benzenedimethanol, 1,3-benzenedimethanol, 1,4-benzenedimethanol, 1,2-dimethoxybenzene, 2-ethoxyanisole, 3,5-diethoxytoluene, benzylmercaptan, phenethylmercaptan, 1,2- benzenedimethanethiol, 1,3-benzenedimethanethiol, 1,4-benzenedimethanethiol, nitrobenzene, 1,2-dinitrobenzene, 1,3-dinitrobenzene, 1,4-dinitrobenzene, benzyl chloride, benzyl bromide, trifluoromethoxy, trifluoroethoxy etc.

In group $R_6$, the term heteroaryl refers to any aryl ring containing one or more of heteroatoms selected from N, O, and S, whereas the term heterocyclyl refers to any heterocyclic ring systems.

$R_3$ is,
a) Phenyl or substituted phenyl. Suitable substituted phenyl groups are selected from but not limited to chlorobenzene, bromobenzene, fluorobenzene, 1,2-dichlorobenzene, 1,2-dibromobenzene, 1,2-difluorobenzene, 1,3-dichlorobenzene, 1,3-dibromobenzene, 1,3-difluorobenzene, 1,4-difluorobenzene, 1,4-dibromobenzene, 1,4-difluorobenzene, methylbenzene, ethylbenzene, o-xylene, m-xylene, p-xylene, 2-ethyl toluene, 3-ethyl toluene, 4-ethyl toluene, propyl benzene, cumene, butyl benzene, sec-butyl benzene, iso-butyl benzene, tert-butyl benzene, o-cymene, m-cymene, p-cymene, 1,2-diethyl benzene, 1,3-diethyl benzene, 1,4-diethylbenzene, 1,3-di-tert-butyl benzene, 1,4-di-tert-butyl benzene, 4-tert butyl toluene, anisole, 2-methyl anisole, 3-methyl anisole, 4-methyl anisole, 1,2-benzenedimethanol, 1,3-benzenedimethanol, 1,4-benzenedimethanol, 1,2-dimethoxybenzene, 2-ethoxyanisole, 3,5-diethoxytoluene, benzylmercaptan, phenethylmercaptan, 1,2-benzenedimethanethiol, 1,3-benzenedimethanethiol, 1,4-benzenedimethanethiol, nitrobenzene, 1,2-dinitrobenzene, 1,3-dinitrobenzene, 1,4-dinitrobenzene, benzyl chloride, benzyl bromide, trifluoromethoxy, trifluoroethoxy etc., or
b) an aryl group, or
c) an unsubstituted or substituted heteroaryl, as defined hereinearlier.

$R_4$ and $R_5$ are each independently i) hydrogen, or ii) a group of formula —$(CH_2)_n$—$R_7$ wherein n=1-3 and $R_7$ is selected from the groups

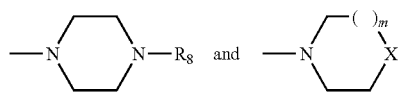

wherein, $R_8$ is
a) phenyl which is unsubstituted or substituted with 1 or 2 substituents each independently selected from the group consisting of halogen, $C_1$-$C_4$ alkyl, $C_1$-$C_4$ alkoxy, $C_1$-$C_4$ thioalkoxy, nitro, amino, haloalkyl, haloalkoxy, wherein the substituents are as defined hereinearlier, or
b) unsubstituted or substituted benzyl; unsubstituted or substituted heteroaryl; unsubstituted or substituted heteroaroyl; unsubstituted or substituted diphenylmethyl, wherein
m=0-2, and
X=—$NCH_3$, $CH_2$, S, SO, or $SO_2$.

Furthermore, the compound of formula (I) of this invention includes its pharmaceutically acceptable, non-toxic, acid addition salts formed with inorganic or organic acids by methods well known in the art. These salts may be used in place of the free bases. Examples of suitable acids for formation of such acid addition salts are maleic, fumaric, benzoic, ascorbic, pamoic, succinic, bismethylene, salicylic, methanesulphonic ethanedisulphonic, acetic, propionic, tartaric, citric, gluconic, aspartic, stearic, palmitic, itaconic, glycolic, p-aminobenzoic, glutamic, benzenesulfinic, phosphoric, hydrobromic, sulfuric, hydrochloric, and nitric acids, and the like.

The present invention also includes the possible tautomers, enantiomers, diastereomers, N-oxides, polymorphs of compound of formula (I), having the same activity.

The present invention also provides pharmaceutical compositions containing compound of formula (I), for the treatment of *M. tuberculosis*. These compositions comprise an effective amount of compound of formula (I), or its tautomers, enantiomers, diastereomers, N-oxides, pharmaceutically acceptable salts or polymorphic forms thereof, in combination with a pharmaceutically acceptable carrier and optionally in the presence of excipients.

Some preferred specific novel compounds No. 1-91 of formula (I) (named according to IUPAC or CAS nomenclature) that form part of this invention are named hereunder:

1. 1-{[1,5-bis(4-chlorophenyl)-2-methylpyrrol-3-yl]methyl}-4-(4-fluorophenyl)piperazine
2. 1-{[1,5-bis(4-chlorophenyl)-2-methylpyrrol-3-yl]methyl}-4-(2-methoxyphenyl)piperazine
3. 1-{[1,5-bis(4-chlorophenyl)-2-methylpyrrol-3-yl]methyl}-4-(3-trifluoro-methylphenyl)piperazine
4. 1-{[1,5-bis(4-chlorophenyl)-2-methylpyrrol-3-yl]methyl}-4-(2-pyridyl)piperazine
5. 1-{[1,5-bis(4-chlorophenyl)-2-methylpyrrol-3-yl]methyl}-4-(2-pyrimidyl)piperazine
6. 1-{[1,5-bis(4-chlorophenyl)-2-methylpyrrol-3-yl]methyl}-4-(diphenylmethyl)piperazine
7. 4-{[1,5-bis(4-chlorophenyl)-2-methylpyrrol-3-yl]methyl}piperazinyl-2-furyl-ketone
8. 5-[(4-{[1,5-bis(4-chlorophenyl)-2-methylpyrrol-3-yl]methyl}piperazinyl)methyl]-2H-benzo[d] 1,3-dioxolane
9. 4-{[1,5-bis(4-chlorophenyl)-2-methylpyrrol-3-yl]methyl}piperazinyloxolan-2-yl-ketone
10. 1-{[1,5-bis(4-chlorophenyl)-2-methylpyrrol-3-yl]methyl}-4-(5-chloro-2-methylphenyl)piperazine
11. N-(3-{[4-(4-fluorophenyl)piperazinyl]methyl}-2-methyl-5-phenylpyrrolyl)-4-pyridylcarboxamide
12. N-(3-{[4-(3-trifluoromethylphenyl)piperazinyl]methyl}-2-methyl-5-phenyl-pyrrolyl)-4-pyridylcarboxamide
13. N-(3-{[4-(2-methoxyphenyl)piperazinyl]methyl}-2-methyl-5-phenylpyrrolyl)-4-pyridylcarboxamide
14. N-(3-{[4-(2-pyridyl)piperazinyl]methyl}-2-methyl-5-phenylpyrrolyl)-4-pyridylcarboxamide
15. N-(2-methyl-5-phenyl-3-{[4-benzylpiperazinyl]methyl}pyrrolyl)-4-pyridyl-carboxamide
16. N-{2-methyl-3-[(4-methylpiperazinyl)methyl]-5-phenylpyrrolyl}-4-pyridyl-carboxamide
17. N-(3-{[4-(2H-benzo[d] 1,3-dioxolan-5-ylmethyl)piperazinyl]methyl}-2-methyl-5-phenylpyrrolyl)-4-pyridylcarboxamide
18. N-(2-methyl-5-phenyl-3-(piperidinylmethyl)pyrrolyl]-4-pyridylcarboxamide
19. N-[2-methyl-5-phenyl-3-(pyrrolidinylmethyl)pyrrolyl]-4-pyridylcarboxamide
20. N-[2-methyl-3-(morpholin-4-ylmethyl)-5-phenylpyrrolyl]-4-pyridyl-carboxamide
21. N-[2-methyl-5-phenyl-3-(1,4-thiazaperhydroin-4-ylmethyl)pyrrolyl]-4-pyridyl carboxamide
22. N-(3-{[4-(4-fluorophenyl)piperazinyl]methyl}-5-methyl-2-phenylpyrrolyl)-4-pyridylcarboxamide
23. N-(3-{[4-(3-trifluoromethylphenyl)piperazinyl]methyl}-5-methyl-2-phenyl pyrrolyl)-4-pyridylcarboxamide 24. N-(3-{[4-(2H-benzo[d] 1,3-dioxolan-5-ylmethyl)piperazinyl]methyl}-5-methyl-2-phenylpyrrolyl)-4-pyridylcarboxamide
25. N-(3-{[4-(4-fluorophenyl)piperazinyl]methyl}-2-methyl-5-phenylpyrrolyl)pyrazin-2-ylcarboxamide
26. N-(3-{[4-(2-methoxyphenyl)piperazinyl]methyl}-2-methyl-5-phenylpyrrolyl)pyrazin-2-ylcarboxamide
27. N-(3-{[4-(3-trifluoromethylphenyl)piperazinyl]methyl}-2-methyl-5-phenylpyrrolyl)pyrazin-2-ylcarboxamide
28. N-(3-{[4-(2-pyridyl)piperazinyl]methyl}-2-methyl-5-phenylpyrrolyl)pyrazin-2-ylcarboxamide
29. N-(3-{[4-(2H-benzo[d] 1,3-dioxolen-5-ylmethyl)piperazinyl]methyl}-2-methyl-5-phenylpyrrolyl)pyrazin-2-ylcarboxamide
30. N-(3-{[4-(diphenylmethyl)piperazinyl]methyl}-2-methyl-5-phenylpyrrolyl)-pyrazin-2-ylcarboxamide
31. N-(3-{[4-(4-fluorophenyl)piperazinyl]methyl}-5-methyl-2-phenylpyrrolyl)pyrazin-2-ylcarboxamide
32. N-(3-{[4-(2-methoxyphenyl)piperazinyl]methyl}-5-methyl-2-phenylpyrrolyl)pyrazin-2-ylcarboxamide
33. N-(3-{[4-(3-trifluoromethylphenyl)piperazinyl]methyl}-5-methyl-2-phenyl pyrrolyl)pyrazin-2-ylcarboxamide
34. N-(3-{[4-(2-pyridyl)piperazinyl]methyl}-5-methyl-2-phenylpyrrolyl)pyrazin-2-ylcarboxamide
35. N-(3-{[4-(2H-benzo[3,4-d]1,3-dioxolan-5-ylmethyl)piperazinyl]methyl}-5-methyl-2-phenylpyrrolyl)pyrazin-2-ylcarboxamide
36. N-(3-{[4-(diphenylmethyl)piperazinyl]methyl}-5-methyl-2-phenylpyrrolyl)pyrazin-2-ylcarboxamide
37. N-(5-(4-chlorophenyl)-3-{[4-(4-fluorophenyl)piperazinyl]methyl}-2-methylpyrrolyl)pyrazin-2-ylcarboxamide
38. N-(5-(4-chlorophenyl)-3-{[4-(2-methoxyphenyl)piperazinyl]methyl}-2-methylpyrrolyl)pyrazin-2-ylcarboxamide
39. N-(5-(4-chlorophenyl)-3-{[4-(3-trifluoromethylphenyl) piperazinyl]methyl}-2-methylpyrrolyl)pyrazin-2-ylcarboxamide
40. N-(5-(4-chlorophenyl)-3-{[4-(2-pyridyl)piperazinyl]methyl}-2-methylpyrrolyl)pyrazin-2-ylcarboxamide
41. N-(2-(4-chlorophenyl)-3-{[4-(4-fluorophenyl)piperazinyl]methyl}-5-methyl pyrrolyl)pyrazin-2-ylcarboxamide
42. N-(2-(4-chlorophenyl)-3-{[4-(2-methoxyphenyl)piperazinyl]methyl}-5-methylpyrrolyl)pyrazin-2-ylcarboxamide
43. N-(2-(4-chlorophenyl)-3-{[4-(3-trifluoromethylphenyl) piperazinyl]methyl}-5-methylpyrrolyl)pyrazin-2-ylcarboxamide
44. 1-{[1-(2,4-difluorophenyl)-5-(4-chlorophenyl)-2-methylpyrrol-3-yl]methyl}-4-(4-fluorophenyl)piperazine
45. 1-{[1-(2,4-difluorophenyl)-5-(4-chlorophenyl)-2-methylpyrrol-3-yl]methyl}-4-(2-methoxyphenyl)piperazine
46. 1-{[1-(2,4-difluorophenyl)-5-(4-chlorophenyl)-2-methylpyrrol-3-yl]methyl}-4-(3-trifluoromethylphenyl)piperazine
47. 1-{[1-(2,4-difluorophenyl)-5-(4-chlorophenyl)-2-methylpyrrol-3-yl]methyl}-4-(2-pyridyl)piperazine
48. 1-{[1-(2,4-difluorophenyl)-5-(4-chlorophenyl)-2-methylpyrrol-3-yl]methyl}-4-(4-diphenylmethyl)piperazine
49. 1-{[1-(2,4-difluorophenyl)-2-(4-chlorophenyl)-5-methylpyrrol-3-yl]methyl}-4-(diphenylmethyl)piperazine
50. 5-[(4-{[1-(2,4-difluorophenyl)-5-(4-chlorophenyl)-2-methylpyrrol-3-yl]-methyl}-piperazinyl)methyl]-2H-benzo[d] 1,3-dioxolane
51. 1-{[1-(2,4-difluorophenyl)-2-methyl-5-phenylpyrrol-3-yl]methyl}-4-(4-fluoro phenyl)piperazine
52. 1-{[1-(2,4-difluorophenyl)-2-methyl-5-phenylpyrrol-3-yl]methyl}-4-(2-methoxy phenyl)piperazine
53. 1-{[1-(2,4-difluorophenyl)-2-methyl-5-phenylpyrrol-3-yl]methyl}-4-(3-trifluoro methylphenyl)piperazine
54. 1-{[1-(2,4-difluorophenyl)-2-methyl-5-phenylpyrrol-3-yl]methyl}-4-(2-pyridyl)piperazine
55. 1-{[1-(2,4-difluorophenyl)-5-methyl-2-phenylpyrrol-3-yl]methyl}-4-(4-fluoro phenyl)piperazine
56. 1-{[1-(2,4-difluorophenyl)-5-methyl-2-phenylpyrrol-3-yl]methyl}-4-(2-methoxy phenyl)piperazine
57. 1-{[1-(2,4-difluorophenyl)-5-methyl-2-phenylpyrrol-3-yl]methyl}-4-(3-trifluoro methylphenyl)piperazine
58. 1-{[1-(2,4-difluorophenyl)-5-methyl-2-phenylpyrrol-3-yl]methyl}-4-(2-pyridyl)piperazine
59. 1-{[5-(4-chlorophenyl)-2-methyl-1-naphthylpyrrol-3-yl]methyl}-4-(2-methoxy phenyl)piperazine
60. 1-{[5-(4-chlorophenyl)-2-methyl-1-naphthylpyrrol-3-yl]methyl}-4-(3-trifluoro-methylphenyl)piperazine
61. 1-{[5-(4-chlorophenyl)-2-methyl-1-naphthylpyrrol-3-yl]methyl}-4-(2-pyridyl)piperazine
62. 5-[(4-{[5-(4-chlorophenyl)-2-methyl-1-naphthylpyrrol-3-yl]methyl}-piperazinyl)methyl]-2H-benzo[d] 1,3-dioxolane
63. 1-{[2-(4-chlorophenyl)-5-methyl-1-naphthylpyrrol-3-yl]methyl}-4-(2-methoxy phenyl)piperazine
64. 1-{[2-(4-chlorophenyl)-5-methyl-1-naphthylpyrrol-3-yl]methyl}-4-(3-trifluoro methylphenyl)piperazine
65. 1-{[2-(4-chlorophenyl)-5-methyl-1-naphthylpyrrol-3-yl]methyl}-4-(2-pyridyl)piperazine
66. N-(5-(4-chlorophenyl)-3-{[4-(4-fluorophenyl)piperazinyl]methyl}-2-methyl pyrrolyl)-4-pyridylcarboxamide
67. N-(5-(4-chlorophenyl)-3-{[4-(2-methoxyphenyl)piperazinyl]methyl}-2-methyl pyrrolyl)-4-pyridylcarboxamide
68. N-(5-(4-chlorophenyl)-3-{[4-(3-trifluoromethylphenyl) piperazinyl]methyl}-2-methylpyrrolyl)-4-pyridylcarboxamide
69. N-(5-(4-chlorophenyl)-3-{[4-(2-pyridyl)piperazinyl]methyl}-2-methylpyrrolyl)-4-pyridylcarboxamide
70. N-(3-{[4-(2H-benzo[d] 1,3-dioxolan-5-ylmethyl)piperazinyl]methyl}-5-(4-chloro-phenyl)-2-methylpyrrolyl)-4-pyridylcarboxamide
71. N-(2-(4-chlorophenyl)-3-{[4-(4-fluorophenyl)piperazinyl]methyl}-5-methyl pyrrolyl)-4-pyridylcarboxamide
72. N-(2-(4-chlorophenyl)-3-{[4-(2-methoxyphenyl)piperazinyl]methyl}-5-methyl pyrrolyl)-4-pyridylcarboxamide
73. N-(2-(4-chlorophenyl)-3-{[4-(3-trifluoromethylphenyl) piperazinyl]methyl}-5-methylpyrrolyl)-4-pyridylcarboxamide
74. N-(2-(4-chlorophenyl)-3-{[4-(2-pyridyl)piperazinyl]methyl}-5-methylpyrrolyl)-4-pyridylcarboxamide
75. N-(3-{[4-(2H-benzo[-d] 1,3-dioxolan-5-ylmethyl)piperazinyl]methyl}-2-(4-chlorophenyl)-5-methylpyrrolyl)-4-pyridylcarboxamide
76. 4-(4-fluorophenyl)-1-[(2-methyl-5-phenyl-1-(2-pyridyl)pyrrol-3-yl)methyl]-piperazine
77. 4-(2-methoxyphenyl)-1-[(2-methyl-5-phenyl-1-(2-pyridyl)pyrrol-3-yl)methyl]-piperazine
78. 4-(3-trifluoromethylphenyl)-1-[(2-methyl-5-phenyl-1-(2-pyridyl)pyrrol-3-yl)-methyl]piperazine
79. 1-[2-methyl-5-phenyl-1-(2-pyridyl)pyrrol-3-yl)methyl]-4-(2-pyridyl)piperazine
80. S-({4-[(2-methyl-5-phenyl-1-(2-pyridyl)pyrrol-3-yl)methyl]piperazinyl} methyl)-2H-benzo[d] 1,3-dioxolane
81. 4-(4-fluorophenyl)-1-[(5-methyl-2-phenyl-1-(2-pyridyl)pyrrol-3-yl)methyl]-piperazine
82. 4-(2-methoxyphenyl)-1-[(5-methyl-2-phenyl-1-(2-pyridyl)pyrrol-3-yl)methyl]-piperazine
83. 4-(3-trifluoromethylphenyl)-1-[(5-methyl-2-phenyl-1-(2-pyridyl)pyrrol-3-yl)-methyl]piperazine 84. 1-[(5-methyl-2-phenyl-1-(2-pyridyl)pyrrol-3-yl)methyl]-4-(2-pyridyl)piperazine
85. 5-({4-[(5-methyl-2-phenyl-1-(2-pyridyl)pyrrol-3-yl)methyl]piperazinyl}-methyl)$_2$H-benzo[d] 1,3-dioxolane
86. 1-{[1,5-bis(4-chlorophenyl)-2-ethylpyrrol-3-yl]methyl}-4-(3-trifluoromethyl-phenyl)piperazine
87. 4-[(2-methyl-1,5-diphenylpyrrol-3-yl)methyl] 1,4-thiazaperhydroin-1-one
88. 4-[(2-methyl-1,5-diphenylpyrrol-3-yl)methyl]-(1,4-thiazaperhydroin-1,1-dione
89. N-[5-(4-chlorophenyl)-2-methyl-3-(1,4-thiazaperhydroin-4-ylmethyl)pyrrolyl]-4-pyridylcarboxamide
90. 2-[3-(hydroxymethyl)-5-methyl-2-phenyl-4-(1,4-thiazaperhydroin-4-ylmethyl)-pyrrolyl]butan-1-ol
91. 2-[2-methyl-5-phenyl-3-(1,4-thiazaperhydroin-4-ylmethyl)pyrrolyl]butan-1-ol The above compounds of Formula I their pharmaceutically acceptable acid salts, thereof and the various possible tautomers, enantiomers, diastereomers, N-oxides and polymorphs thereof are all found to be pharmaceutically active especially in treatment of mycobacterial conditions such as *Mycobacterium tuberculosis*, drug resistant, *Mycobacterium tuberculosis, Mycobacterium avium-intracellulare* complex, *Mycobacterium fortuitum* or *mycobacterium kansasii*.

The pharmaceutically active compounds of formula (I) of this invention can be prepared by any one of the methods given below:

Method-I:

Scheme-I shows the synthesis of compounds of the Formula (I) in which $R_1$ is $CH_3$, $R_3$ designates substituted or unsubstituted phenyl groups and $R_2$, $R_4$ and $R_5$ are as defined earlier. The method comprises condensation compound, $R_3H$ of the formula (II) with acid chloride of formula (II), in the presence of $AlCl_3$ at a temperature ranging from 20-30° C. for a period varying between 1-2 hours to produce diketones of formula (IV), which on condensation with appropriate amines ($R_2$—$NH_2$) followed by cyclisation in the presence of an organic solvent at a temperature ranging between 80-120° C. for a period varying between 2-3 hours gives the corresponding pyrroles of the formula (V), as described by M. Biava et. al. in *Bioorg. & Med. Chem. Lett.*, 1999, 9, 2983-2988. The compounds of the formula (V) on reaction with various heterocyclic amines ($R_7H$) in presence of an organic solvent at a temperature ranging from 20-30° C. for a period varying between 2-4 hours afford compounds of formula (I), wherein $R_1$, $R_2$, $R_3$, $R_4$, and $R_5$ have the same meanings as defined hereinabove.

The starting acid chlorides of the formula (III) are known in the art and may be synthesized by the procedure described by Bui-Hoi, N. P. in *J. Org. Chem.*, 1960, 25, 390.

Scheme- I:
Synthesis of compound of formula (I)

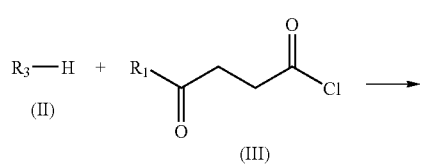

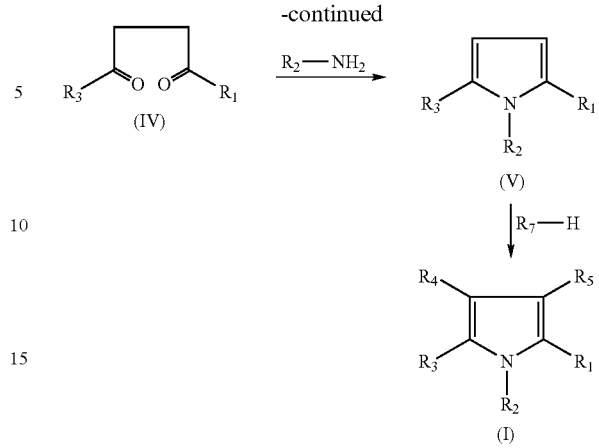

Method-II:

In this method, summarized in Scheme-II, methyl ketones of formula (VI) are condensed with α-Bromomethyl ketones of formula (VII), in the presence of a base and an organic solvent at a temperature ranging from 20-30° C. for a period varying between 2-6 days to produce diketones of formula (IV), which on condensation with appropriate amines ($R_2$—$NH_2$) followed by cyclisation in the presence of an organic solvent at a temperature ranging between 80-120° C. for a period varying between 2-3 hours give corresponding pyrroles of the formula (V). Reaction of compounds of the formula (V) with various amines ($R_7H$) in presence of an organic solvent at a temperature ranging from 20-30° C. for period varying between 2-4 hours afford compounds of formula (I), wherein $R_1$, $R_2$, $R_3$, $R_4$, and $R_5$ have the same meanings as defined hereinabove.

Scheme- II:
Synthesis of compound of formula (I)

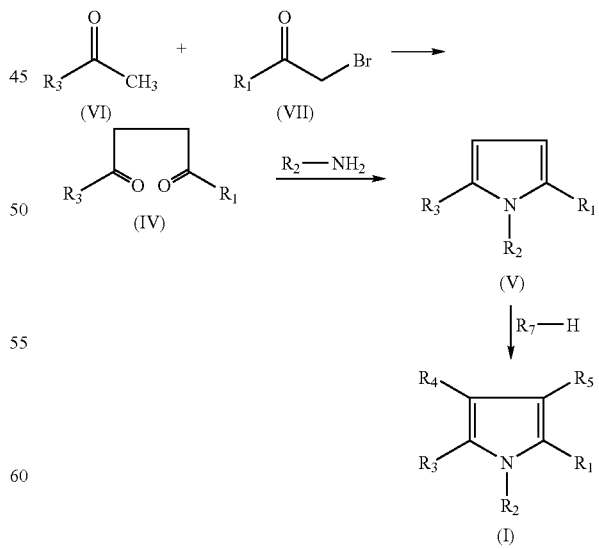

In the above Schemes, where specific bases, acids, solvents etc., are mentioned, it is to be understood that other acids, bases solvents etc., known to those skilled in the art may also be used. Similarly, the reaction temperature and duration of the reactions may be adjusted according to the desired needs.

While the invention has been described by reference to specific embodiments, this is for purposes of illustration only. Numerous alternative embodiments will be apparent to those skilled in the art and are deemed to be within the scope of the invention.

The following examples demonstrate the general as well as the specific preparation of compounds embodied in formula (I), which, however, should not be construed as to limiting the scope of the invention.

EXAMPLE-1

Preparation of 1-{[1,5-bis(4-chlorophenyl)-2-methylpyrrol-3-yl]methyl}-4-(3-trifluoro-methyl phenyl)piperazine (Compound No. 3 of Formula I) as per Method-I Step 1: 1-(4-chlorophenyl)pentane-1,4-dione To a well stirred suspension of anhydrous aluminium chloride (29.66 g, 0.223 mol) in 154.7 ml of chlorobenzene was added 4-oxopentanoylchloride (25.0 g, 0.187 mol) drop-wise, over a period of 30-35 minutes at room temperature (25-30° C.). The reaction mixture was stirred at the same temperature for 1 hour. After decomposition of the reaction mixture by the addition of solid ice and hydrochloric acid (10 ml) the precipitated solid was filtered and filtrate was concentrated in a rotary evaporation to remove all the solvents. The residue was dissolved in ethyl acetate (400 ml), washed with water (2×100 ml), brine (100 ml). The organic layer was dried over anhydrous sodium sulfate and the solvent evaporated off. The crude product so obtained was chromatographed over silica gel (100-200 mesh) using chloroform-hexane (90:10) as eluent to give 5.3 g (13.60%) of the title compound.

Step-2: 1,2-bis-(4-chlorophenyl)-5-methylpyrrole

A mixture of 1-(4-chlorophenyl)pentane-1,4-dione (5.0 g., 0.024 mol, as obtained in Step-1) and 4-chloroaniline (3.33 g, 0.026 mol) in benzene (5.0 ml) was refluxed either over molecular sieves or using a Dean Stark apparatus. After three hours, benzene was removed under reduced pressure and the residue dissolved in ethyl acetate, washed with water (2×100 ml.) and brine (1×50 ml). The ethyl acetate layer was dried over anhydrous sodium sulfate, and the solvent evaporated off. The solid so obtained was washed with hexane to give 2.83 g (39.45%) of the title compound.

Step-3: 1-{[1,5-bis(4-chlorophenyl)-2-methylpyrrol-3-yl]methyl}-4-(3-trifluoromethyl phenyl)piperazine To a stirred solution of 1,2-bis(4-chlorophenyl)-5-methylpyrrole (1.76 g, 0.006 mol, as obtained in Step-2) in acetonitrile (18 ml) was added a mixture of 1-(3-trifluoromethylphenyl)piperazine hydrochloride (1.55 g, 0.006 mol), 40% formaldehyde (0.45 ml, 0.006 mol) and acetic acid (5.23 ml) drop-wise. After the completion of addition, the reaction mixture was stirred at room temperature for 3-4 hours. The reaction mixture was neutralized with NaOH (20% aq. soln.) and extracted with ethyl acetate (2×100 ml). The combined ethyl acetate extract was washed with water (2×50 ml), brine (1×30 ml), dried over anhydrous sodium sulfate and the solvent evaporated off. The crude product so obtained was purified by column chromatography over silica gel using ethyl acetate hexane (80:10) as eluent to give 2.1 g (66.24%) of the title compound.

m.p. 165-167° C., MS: m/z 544 (M+1)

$^1$HNMR (CDCl$_3$, δ): 2.05 (s, 3H, C$\underline{H}_3$), 2.77 (br s, 4H, 2xN—C$\underline{H}_2$), 3.31 (br s, 4H, 2xN—C$\underline{H}_2$), 3.59 (s, 2H, N—C$\underline{H}_2$), 6.34 (s, 1H, $\underline{H}$-4), 6.85-7.31 (m, 12H, Ar—$\underline{H}$).

EXAMPLE-2

Preparation of N-(3-{[4-(3-trifluoromethylphenyl)piperazinyl]methyl}-5-methyl-2-phenylpyrrolyl)-4-pyridylcarboxamide (Compound No. 23 of Formula I) and Preparation of N-(3-{[4-(3-trifluoromethylphenyl)piperazinyl]methyl}-2-methyl-5-phenylpyrrolyl)-4-pyridylcarboxamide (Compound No. 12 of Formula I) as per Method-I Step 1: 1-(phenyl)pentane-1,4-dione To a well stirred suspension of anhydrous aluminium chloride (27.0 g, 205.9 mmol) in 126 ml of benzene was added 4-oxopentanoylchloride (23.0 g, 171.6 mmol) drop-wise, over a period of 30-35 minutes at room temperature (25-30° C.). The reaction mixture was stirred at the same temperature for 1 hour. After decomposition of the reaction mixture by the addition of solid ice and hydrochloric acid (10 ml) the precipitated solid was filtered and the filtrate evaporated on a rotary evaporator to remove all the solvents. The residue was dissolved in ethyl acetate (400 ml), washed with water (2×100 ml), brine (100 ml) and dried over anhydrous sodium sulfate and the solvent evaporated off. The crude product so obtained was chromatographed over silica gel (100-200 mesh) using chloroform as eluent to give 8.6 g (24.07%) of the title compound.

Step-2: N-(5-methyl-2-phenylpyrrolyl)-4-pyridylcarboxamide

A mixture of 1-(phenyl)pentane-1,4-dione (6.0 g, 28.50 mmol, as obtained in Step-1) and isonicotinic hydrazide (4.30 g, 31.35 mmol) in benzene (6.0 ml) was refluxed by over molecular sieves. After two hours, benzene was removed under reduced pressure and the residue dissolved in ethyl acetate, washed with water (2×100 ml) and brine (1×50 ml). The ethyl acetate layer was dried over anhydrous sodium sulfate and the solvent evaporated off. The crude product so obtained was purified by column chromatography over silica gel (100-200 mesh) using 0.2% methanol in chloroform as eluent to give 3.50 g (39.42%) of the title compound.

Step-3: N-(3-{[4-(3-trifluoromethylphenyl)piperazinyl]methyl}-5-methyl-2-phenyl pyrrolyl)-4-pyridylcarboxamide (compound No. 23 of Formula I) and N-(3-{[4-(3-trifluoromethylphenyl)piperazinyl]methyl}-2-methyl-5-phenylpyrrolyl)-4-pyridylcarboxamide (compound No. 12 of Formula I)

To a stirred solution of N-(5-methyl-2-phenylpyrrolyl)-4-pyridylcarboxamide (0.300 g, 1.083 mmol, as obtained in Step-2) in acetonitrile (5.0 ml) was added a mixture of 1-(3-trifluoromethylphenyl)piperazine hydrochloride (0.288 g, 1.083 mmol), 40% formaldehyde (0.032 g, 1.083 mmol) and acetic acid (0.09 ml), drop-wise. After the completion of addition, the reaction mixture was stirred at room temperature for 4 hours. The reaction mixture was neutralized with sodium hydroxide (20% aq. Soln.) and extracted with ethyl acetate (2×50 ml). The combined ethyl acetate extract was washed with water (2×25 ml), brine (1×20 ml), and dried over anhydrous sodium sulfate and the solvent evaporated off.

TLC of the crude product indicated two spots, which were separated by column chromatography over silica gel (100-200 mesh).

The less polar compound eluted out using 60% ethyl acetate-hexane mixture was obtained in 11.25% (0.060 g) yield and was identified as N-(3-{[4-(3-trifluoromethylphenyl)piperazinyl]methyl}-5-methyl-2-phenylpyrrolyl)-4-pyridyl-carboxamide (Compound 23).

m.p. 105-107° C., MS: m/z 520 (M+1)

$^1$H NMR (CDCl$_3$, δ): 2.14 (s, 3H, CH$_3$), 2.49 (br s, 4H, 2xN—CH$_2$), 3.12 (br s, 4H, 2xN—CH$_2$), 3.34 (s, 2H, N—CH$_2$), 6.03 (s, 1H, H-3), 6.96-6.99 (m, 4H, ArH), 7.09-7.27 (m, 5H, ArH), 7.40 (d, 2H, J=6 Hz, pyridyl ring), 8.60 (d, 2H, J=6 Hz, pyridyl ring).

The more polar compound eluted out using 80% ethyl acetate-hexane mixture was obtained in 24.34% yield (0.130 g) and was identified as N-(3-{[4-(3-trifluoromethylphenyl)piperazinyl]methyl}-2-methyl-5-phenylpyrrolyl)-4-pyridyl-carboxamide (Compound 12)

m.p. 80-82° C., MS: m/z 520 (M+1)

$^1$H NMR (CDCl$_3$, δ): 2.13 (s, 3H, CH$_3$), 2.60 (br s, 4H, 2xN—CH$_9$), 3.18 (bs, 4H, 2xN—CH$_2$), 3.41 (s, 2H, N—CH$_2$), 6.24 (s, 1H, H-4), 6.97-7.03 (4H, m, ArH), 7.22-7.29 (m, 5H, ArH), 7.53 (d, 2H, J=6 Hz, pyridyl ring), 8.50 (br s, 1H, NH D$_2$O exchangeable), 8.70 (d, 2H, J=6 Hz, pyridyl ring).

EXAMPLE-3

Preparation of 1-{[1,5-bis(4-chlorophenyl)-2-ethylpyrrol-3-yl]methyl}-4-(3-trifluoro-methylphenyl)piperazine (Compound No. 86 of Formula I) as per Method-II Step 1: 1-(4-chlorophenyl)hexane-1,4-dione Anhydrous zinc chloride (3.71 g, 27.2 mmol) was placed into a round bottom flask and dried by melting under vacuum at 250-350° C. for 15 minutes. After cooling under vacuum to room temperature, benzene (15 ml.), triethylamine (2.7 ml, 19.42 mmol) and tert-butanol (1.83 ml, 19.42 mmol) were successively added. The mixture was stirred until zinc chloride was fully dissolved (approx. 2 hour) and 1-(4-chlorophenyl)ethan-1-one (3.0 g, 19.42 mmol) and 1-bromobutan-2-one (2.05 g, 13.6 mmol) were successively added. The mixture was stirred for 1 hour and allowed to stand for 4 days at room temperature, and thereafter quenched with 5% aq. sulfuric acid. The organic layer was separated, washed with water (2×50 ml), brine (1×25 ml), dried over anhydrous sodium sulfate and the solvent evaporated off. The crude product was purified by column chromatography over silica gel (100-200 mesh) using chloroform as eluent to give 2.30 g (75.63%) of the title compound.

Step-2: 1,2-bis(4-chlorophenyl)-5-ethylpyrrole

A mixture of 1-(4-chlorophenyl)hexane-1,4-dione (2.10 g, 9.35 mmol, as obtained in Step-1), 4-chloro aniline (1.31 g, 10.29 mmol), and p-toluene sulfonic acid (0.321 g, 1.80 mmol) in toluene (5.0 ml) was refluxed over molecular sieves or using a Dean Stark apparatus. The progress of the reaction was monitored by TLC and after three hours, toluene was removed under reduced pressure. The residue was dissolved in ethyl acetate (200 ml), washed with aqueous sodium bicarbonate solution (2×75 ml), followed by washing with water (2×50 ml) and brine (1×25 ml). The ethyl acetate layer was dried over anhydrous sodium sulfate and the solvent evaporated off. The solid so obtained was washed with hexane to give 2.39 g (81%) of the title compound.

Step-3: 1-{[1,5-bis(4-chlorophenyl)-2-ethylpyrrol-3-yl]methyl}-4-(3-trifluoromethyl-phenyl)piperazine To a stirred solution of 1,2-bis(4-chlorophenyl)-5-ethylpyrrole (1.20 g, 3.80 mmol, as obtained in Step-2) in acetonitrile (15 ml.) was added a mixture of 1-(3-trifluoromethylphenyl)piperazine hydrochloride (1.01 g, 3.80 mmol), 40% formaldehyde (0.114 g, 3.80 mmol) and acetic acid (3.6 ml), drop-wise. After the completion of addition, the reaction mixture was stirred at room temperature for 3 hours. The reaction mixture was neutralized with sodium hydroxide (20% aq. solution) and extracted with ethyl acetate (2×100 ml). The combined ethyl acetate extract was washed with water (2×50 ml), brine (1×30 ml), dried over anhydrous sodium sulfate and the solvent evaporated off. The crude product so obtained was chromatographed over silica gel using ethyl acetate-hexane (80:10) as eluent to give 1.05 gm (47.22%) of 1-{[1,5-bis(4-chlorophenyl)-2-ethylpyrrol-3-yl]methyl}-4-(3-trifluoro-methylphenyl)piperazine (Compound No. 86 of Formula I).

MS: m/z 559 (M+1)

$^1$HNMR (CDCl$_3$, δ): 1.05 (t, 3H, CH$_3$), 2.66 (q, 2H, J=8 Hz, CH2CH3), 2.98-3.10 (br s, 4H, 2xN—CH$_2$), 3.50-3.55 (br s, 4H, 2xN—CH$_2$), 3.94 (s, 2H, N—CH$_2$), 6.50 (s, 1H, H-4), 7.20-7.38 (m, 12H, Ar—H).

EXAMPLE-4

Preparation of Hydrochloride Salt of Compound No. 3 of Formula I

The compound No. 3 (1.1 gm) as obtained in Step-3 of Example-1 was dissolved in dichloromethane (3 ml) under stirring. To this mixture 6.43 M HCl-Ethanol (295.22 mg, 8.08 mmoles, 1.3 ml, 4 equivalent) was added drop-wise under stirring at 10° C. The reaction mixture was stirred for additional 2 minutes and was diluted with diethyl ether (10 ml.). Stirring was continued for another 15 minutes at the same temperature. The solvents were evaporated at reduced pressure and solid was dried in vacuum desiccator for 1 hour to give 1.22 g of the title hydrochloride salt.

m.p. 140-142° C.

$^1$H NMR (DMSOd$_6$, δ): 2.03 (s, 3H, CH$_3$, 3.10 (br s, 4H, 2xN—CH$_2$), 3.91 (br s, 4H, 2xN—CH$_2$) 4.17 (s, 2H, N—CH$_2$), 6.57 (s, 1H, H-4), 6.91-7.48 (m, 12H, ArH).

EXAMPLE-5

Preparation of Hydrochloride Salt of Compound No. 12 of Formula I

The Compound No. 12 (0.405 g), obtained by Step-3 of Example-2 was dissolved in a mixture of diethyl ether (0.5 ml) and dichloromethane (0.5 ml) under stirring. To this mixture 1.20M HCl-Ethereal (142.35 mg., 3.90 mmoles, 3.25 ml, 5 equivalent) was added drop-wise under stirring at 10° C. The reaction mixture was stirred for additional 2 minutes and was diluted with diethyl ether (10 ml.). Stirring was continued for another 15 minutes at the same temperature. The solvents were evaporated at reduced pressure and solid was dried in vacuum desiccator for 1 hour to give 0.428 g of the title hydrochloride salt.

m.p. 174-176° C.

¹H NMR (DMSO d₆, δ): 2.10 (s, 3H, CH₃), 3.15 (br s, 4H, 2xN—CH₂), 3.84 (br s, 4H, 2xN—CH₂), 4.13 (s, 2H, N—CH₂), 6.47 (s, 1H, H-4), 7.00-7.38 (m, 8H, ArH), 7.85 (d, 2H, J=6 Hz, pyridyl ring), 8.76 (d, 2H, J=6 Hz, pyridyl ring).

An illustrative list of the compounds of the invention which were synthesized by one or more of the above described methods is now given below.

EXAMPLE-6

By utilization of the procedure described in Examples 1-3, Compound Nos. 1-2, 4-11, 13-22, 24-85, and 87-91 of Formula I were prepared having characteristics detailed hereunder:

1. 1-{[1,5-bis(4-chlorophenyl)-2-methylpyrrol-3-yl]methyl}-4-(4-fluorophenyl)-piperazine; m.p. 193-195° C., MS: m/z 494 (M+1)
2. 1-{[1,5-bis(4-chlorophenyl)-2-methylpyrrol-3-yl]methyl}-4-(2-methoxyphenyl)piperazine; m.p. 140-142° C., MS: m/z 506 (M+1)
4. 1-{[1,5-bis(4-chlorophenyl)-2-methylpyrrol-3-yl]methyl}-4-(2-pyridyl)piperazine; m.p. 152-154° C., MS: m/z 477 (M+1)
5. 1-{[1,5-bis(4-chlorophenyl)-2-methylpyrrol-3-yl]methyl}-4-(2-pyrimidyl)piperazine; m.p. 184-186° C., MS: m/z 478 (M+1)
6. 1-{[1,5-bis(4-chlorophenyl)-2-methylpyrrol-3-yl]methyl}-4-(diphenylmethyl)piperazine; m.p. 188-190° C., MS: m/z 566 (M+1)
7. 4-{[1,5-bis(4-chlorophenyl)-2-methylpyrrol-3-yl]methyl}piperazinyl 2-furylketone; m.p. 84-86° C., MS: m/z 494 (M+1)
8. 5-[(4-{[1,5-bis(4-chlorophenyl)-2-methylpyrrol-3-yl]methyl}piperazinyl)methyl]-2H-benzo[d]1,3-dioxolane; m.p. 135-137° C., MS: m/z 534 (M+1)
9. 4-{[1,5-bis(4-chlorophenyl)-2-methylpyrrol-3-yl]methyl}piperazinyloxolan-2-yl-ketone; m.p. 150-152° C., MS: m/z 498 (M+1)
10. 1-{[1,5-bis(4-chlorophenyl)-2-methylpyrrol-3-yl]methyl}-4-(5-chloro-2-methylphenyl)piperazine; m.p. 156-158° C., MS: m/z 524 (M+1)
11. N-(3-{[4-(4-fluorophenyl)piperazinyl]methyl}-2-methyl-5-phenylpyrrolyl)-4-pyridylcarboxamide; m.p. 98-100° C., MS: m/z 470 (M+1)
13. N-(3-{[4-(2-methoxyphenyl)piperazinyl]methyl}-2-methyl-5-phenylpyrrolyl)-4-pyridylcarboxamide; m.p. 125-128° C., MS: m/z 482 (M+1)
14. N-(3-{[4-(2-pyridyl)piperazinyl]methyl}-2-methyl-5-phenylpyrrolyl)-4-pyridyl carboxamide; m.p. 93-95° C., MS: m/z 453 (M+1)
15. N-(2-methyl-5-phenyl-3-{[4-benzylpiperazinyl]methyl}pyrrolyl)-4-pyridyl carboxamide; m.p. 87-89° C., MS: m/z 466 (M+1)
16. N-{2-methyl-3-[(4-methylpiperazinyl}methyl]-5-phenylpyrrolyl)-4-pyridyl-carboxamide; thick oil, MS: m/z 390 (M+1)
17. N-(3-{[4-(2H-benzo[d] 1,3-dioxolan-5-ylmethyl)piperazinyl]methyl}-2-methyl-5-phenylpyrrolyl)-4-pyridylcarboxamide; m.p. 95-97° C., MS: m/z 510 (M+1)
18. N-[2-methyl-5-phenyl-3-(piperidinylmethyl)pyrrolyl]-4-pyridylcarboxamide; m.p. 98-100° C., MS: m/z 376 (M+1)
19. N-[2-methyl-5-phenyl-3-(pyrrolidinylmethyl)pyrrolyl]-4-pyridylcarboxamide; m.p. 72-73° C., MS: m/z 361 (M+1)
20. N-[2-methyl-3-(morpholin-4-ylmethyl)-5-phenylpyrrolyl]-4-pyridylcarboxamide; m.p. 160-162° C., MS: m/z 377 (M+1)
21. N-(2-methyl-5-phenyl-3-(1,4-thiazaperhydroin-4-ylmethyl)pyrrolyl]-4-pyridyl carboxamide m.p. 87-89° C., MS: m/z 393 (M+1)
22. N-(3-{[4-(4-fluorophenyl)piperazinyl]methyl}-5-methyl-2-phenylpyrrolyl)-4-pyridylcarboxamide; m.p. 98-99° C., MS: m/z 470 (M+1)
24. N-(3-{[4-(2H-benzo[-d] 1,3-dioxolan-5-ylmethyl)piperazinyl]methyl}-5-methyl-2-phenylpyrrolyl)-4-pyridylcarboxamide; m.p. 96-98° C., MS: m/z 510 (M+1)
25. N-(3-{[4-(4-fluorophenyl)piperazinyl]methyl}-2-methyl-5-phenylpyrrolyl)pyrazin-2-ylcarboxamide; m.p. 80-82° C., MS: m/z 471 (M+1)
26. N-(3-{[4-(2-methoxyphenyl)piperazinyl]methyl}-2-methyl-5-phenylpyrrolyl)pyrazin-2-ylcarboxamide; m.p. 76-78° C., MS: m/z 483 (M+1)
27. N-(3-{[4-(3-trifluoromethylphenyl)piperazinyl]methyl}-2-methyl-5-phenyl-pyrrolyl)pyrazin-2-ylcarboxamide; m.p. 83-85° C., MS: m/z 521 (M+1)
28. N-(3-{[4-(2-pyridyl)piperazinyl]methyl}-2-methyl-5-phenylpyrrolyl)pyrazin-2-ylcarboxamide; m.p. 119-121° C., MS: m/z 454 (M+1)
29. N-(3-{[4-(2H-benzo[d] 1,3-dioxolan-5-ylmethyl)piperazinyl]methyl}-2-methyl-5-phenylpyrrolyl)pyrazin-2-ylcarboxamide; m.p. 186-188° C., MS: m/z 511 (M+1)
30. N-(3-{[4-(diphenylmethyl)piperazinyl]methyl}-2-methyl-5-phenylpyrrolyl)pyrazin-2-ylcarboxamide; m.p. 91-93° C., MS: m/z 543 (M+1)
31. N-(3-{[4-(4-fluorophenyl)piperazinyl]methyl}-5-methyl-2-phenylpyrrolyl)pyrazin-2-ylcarboxamide; m.p. 200-202° C., MS: m/z 471 (M+1)
32. N-(3-{[4-(2-methoxyphenyl)piperazinyl]methyl}-5-methyl-2-phenylpyrrolyl)pyrazin-2-ylcarboxamide; m.p. 74-76° C., MS: m/z 483 (M+1)
33. N-(3-{[4-(3-trifluoromethylphenyl)piperazinyl]methyl}-5-methyl-2-phenylpyrrolyl)pyrazin-2-ylcarboxamide; m.p. 231-233° C., MS: m/z 521 (M+1)
34. N-(3-{[4-(2-pyridyl)piperazinyl]methyl}-5-methyl-2-phenylpyrrolyl)pyrazin-2-yl carboxamide; m.p. 208-210° C., MS: m/z 454 (M+1)
35. N-(3-{[4-(2H-benzo[-d] 1,3-dioxolan-5-ylmethyl)piperazinyl]methyl}-5-methyl-2-phenylpyrrolyl)pyrazin-2-ylcarboxamide; m.p. 81-83° C., MS: m/z 511 (M+1)
36. N-(3-{[4-(diphenylmethyl)piperazinyl]methyl}-5-methyl-2-phenylpyrrolyl)pyrazin-2-ylcarboxamide; m.p. 95-97° C., MS: m/z 543 (M+1)
37. N-(5-(4-chlorophenyl)-3-{[4-(4-fluorophenyl)piperazinyl]methyl}-2-methylpyrrolyl)pyrazin-2-ylcarboxamide; m.p. 110-112° C., MS: m/z 505 (M+1)
38. N-(5-(4-chlorophenyl)-3-{[4-(2-methoxyphenyl)piperazinyl]methyl}-2-methylpyrrolyl)pyrazin-2-ylcarboxamide; m.p. 100-102° C., MS: m/z 517 (M+1)
39. N-(5-(4-chlorophenyl)-3-{[4-(3-trifluoromethylphenyl)piperazinyl]methyl}-2-methylpyrrolyl)pyrazin-2-ylcarboxamide; m.p. 96-98° C., MS: m/z 555 (M+1)
40. N-(5-(4-chlorophenyl)-3-{[4-(2-pyridyl)piperazinyl]methyl}-2-methyl pyrrolyl)pyrazin-2-ylcarboxamide; m.p. 104-106° C., MS: m/z 488 (M+1)
41. N-(2-(4-chlorophenyl)-3-{[4-(4-fluorophenyl)piperazinyl]methyl}-5-methyl pyrrolyl)pyrazin-2-ylcarboxamide; m.p. 202-204° C., MS: m/z 505 (M+1)
42. N-(2-(4-chlorophenyl)-3-{[4-(2-methoxyphenyl)piperazinyl]methyl}-5-methyl-pyrrolyl)pyrazin-2-ylcarboxamide; m.p. 96-98° C., MS: m/z 517 (M+1)
43. N-(2-(4-chlorophenyl)-3-{[4-(3-trifluoromethylphenyl)piperazinyl]methyl}-5-methylpyrrolyl)pyrazin-2-ylcarboxamide; m.p. 226-228° C., MS: m/z 555 (M+1)

44. 1-{[1-(2,4-difluorophenyl)-5-(4-chlorophenyl)-2-methylpyrrol-3-yl]methyl}-4(4-fluorophenyl)piperazine; m.p. 132-134° C., MS: m/z 496 (M+1)

45. 1-{[1-(2,4-difluorophenyl)-5-(4-chlorophenyl)-2-methylpyrrol-3-yl]methyl}-4(2-methoxyphenyl)piperazine; m.p. 65-67° C., MS: m/z 508 (M+1)

46. 1-{[1-(2,4-difluorophenyl)-5-(4-chlorophenyl)-2-methylpyrrol-3-yl]methyl}-4(3-trifluoromethylphenyl)piperazine; m.p. 112-114° C., MS: m/z 546 (M+1)

47. 1-{[1-(2,4-difluorophenyl)-5-(4-chlorophenyl)-2-methylpyrrol-3-yl]methyl}-4-(2-pyridyl)piperazine; m.p. 124-126° C., MS: m/z 479 (M+1)

48. 1-{[1-(2,4-difluorophenyl)-5-(4-chlorophenyl)-2-methylpyrrol-3-yl]methyl}-4(4-diphenylmethyl)piperazine; m.p. 70-72° C., MS: m/z 568 (M+1)

49. 1-{[1-(2,4-difluorophenyl)-2-(4-chlorophenyl)-5-methylpyrrol-3-yl]methyl}-4-(diphenylmethyl)piperazine; m.p. 76-78° C., MS: m/z 568 (M+1)

50. 5-[(4-{[1-(2,4-difluorophenyl)-5-(4-chlorophenyl)-2-methylpyrrol-3-yl]methyl}-piperazinyl)methyl]-2H-benzo[d]1,3-dioxolane; thick oil MS: m/z 536 (M+1)

51. 1-{[1-(2,4-difluorophenyl)-2-methyl-5-phenylpyrrol-3-yl]methyl}-4-(4-fluoro-phenyl)piperazine; m.p. 140-142° C., MS: m/z 462 (M+1)

52. 1-{1-[1-(2,4-difluorophenyl)-2-methyl-5-phenylpyrrol-3-yl]methyl}-4-(2-methoxy-phenyl)piperazine; m.p. 64-66° C., MS: m/z 474 (M+1)

53. 1-{[1-(2,4-difluorophenyl)-2-methyl-5-phenylpyrrol-3-yl]methyl}-4-(3-trifluoro-methylphenyl)piperazine; m.p. 122-124° C., MS: m/z 512 (M+1)

54. 1-{[1-(2,4-difluorophenyl)-2-methyl-5-phenylpyrrol-3-yl]methyl}-4-(2-pyridyl)-piperazine; m.p. 144-146° C., MS: m/z 445 (M+1)

55. 1-{[1-(2,4-difluorophenyl)-5-methyl-2-phenylpyrrol-3-yl]methyl}-4-(4-fluoro phenyl)piperazine; thick oil, MS: m/z 462 (M+1)

56. 1-{[1-(2,4-difluorophenyl)-5-methyl-2-phenylpyrrol-3-yl]methyl}-4-(2-methoxy phenyl)piperazine; m.p. 60-62° C., MS: m/z 474 (M+1)

57. 1-{[1-(2,4-difluorophenyl)-5-methyl-2-phenylpyrrol-3-yl]methyl}-4-(3-trifluoro methylphenyl)piperazine; thick oil, MS: m/z 512(M+1)

58. 1-{[1-(2,4-difluorophenyl)-5-methyl-2-phenylpyrrol-3-yl]methyl}-4-(2-pyridyl)piperazine; thick oil, MS: m/z 445(M+1)

59. 1-{[5-(4-chlorophenyl)-2-methyl-1-naphthylpyrrol-3-yl]methyl}-4-(2-methoxy phenyl)piperazine; m.p. 65-67° C., MS: m/z 522 (M+1)

60. 1-{[5-(4-chlorophenyl)-2-methyl-1-naphthylpyrrol-3-yl]methyl}-4-(3-trifluoro-methylphenyl)piperazine; m.p. 68-70° C., MS: m/z 560 (M+1)

61. 1-{[5-(4-chlorophenyl)-2-methyl-1-naphthylpyrrol-3-yl]methyl}-4-(2-pyridyl)piperazine; m.p. 68-70° C., MS: m/z 493

62. 5-[(4-{[5-(4-chlorophenyl)-2-methyl-1-naphthylpyrrol-3-yl]methyl}-piperazinyl)methyl]-2H-benzo[d]1,3-dioxolane; m.p. 70-72° C., MS: m/z 550 (M+1)

63. 1-{[2-(4-chlorophenyl)-5-methyl-1-naphthylpyrrol-3-yl]methyl}-4-(2-methoxy phenyl)piperazine; thick oil, MS: nm/z 522 (M+1)

64. 1-{[2-(4-chlorophenyl)-5-methyl-1-naphthylpyrrol-3-yl]methyl}-4-(3-trifluoro methylphenyl)piperazine; m.p. 78-80° C., MS: m/z 560 (M+1)

65. 1{[2-(4-chlorophenyl)-5-methyl-1-naphthylpyrrol-3-yl]methyl}-4-(2-pyridyl)piperazine; thick oil, MS: m/z 493 (M+1)

66. N-(5-(4-chlorophenyl)-3-{[4-(4-fluorophenyl)piperazinyl]methyl}-2-methylpyrrolyl)-4-pyridylcarboxamide; m.p. 78-80° C., MS: m/z 504 (M+1)

67. N-(5-(4-chlorophenyl)-3-{[4-(2-methoxyphenyl)piperazinyl]methyl}-2-methyl pyrrolyl)-4-pyridylcarboxamide; m.p. 175-177° C., MS: m/z 516 (M+1)

68. N-(5-(4-chlorophenyl)-3-{[4-(3-trifluoromethylphenyl)piperazinyl]methyl}-2-methylpyrrolyl)-4-pyridylcarboxamide; m.p. 119-121° C. MS: m/z 554 (M+1)

69. N-(5-(4-chlorophenyl)-3-{[4-(2-pyridyl)piperazinyl]methyl}-2-methylpyrrolyl)-4-pyridylcarboxamide; thick oil, MS: m/z 487 (M+1)

70. N-(3-{[4-(2H-benzo[d] 1,3-dioxolan-5-ylmethyl)piperazinyl]methyl}-5-(4-chloro phenyl)-2-methylpyrrolyl)-4-pyridylcarboxamide; m.p. 69-71° C., MS: m/z 544 (M+1)

71. N-(2-(4-chlorophenyl)-3-{[4-(4-fluorophenyl)piperazinyl]methyl}-5-methylpyrrolyl)-4-pyridylcarboxamide; m.p. 70-72° C., MS: m/z 504 (M+1)

72. N-(2-(4-chlorophenyl)-3-{[4-(2-methoxyphenyl)piperazinyl]methyl}-5-methyl pyrrolyl)-4-pyridylcarboxamide; m.p. 92-94° C., MS: m/z 516 (M+1)

73. N-(2-(4-chlorophenyl)-3-{[4-(3-trifluoromethylphenyl)piperazinyl]methyl}-5-methylpyrrolyl)-4-pyridylcarboxamide; m.p. 144-146° C., MS: m/z 554 (M+1)

74. N-(2-(4-chlorophenyl)-3-{[4-(2-pyridyl)piperazinyl]methyl}-5-methylpyrrolyl)-4-pyridylcarboxamide; thick oil, MS: m/z 487 (M+1)

75. N-(3-{[4-(2H-benzo[-d] 1,3-dioxolan-5-ylmethyl)piperazinyl]methyl}-2-(4-chlorophenyl)-5-methylpyrrolyl)-4-pyridylcarboxamide; m.p. 65-67° C., MS: m/z 544 (M+1)

76. 4-(4-fluorophenyl)-1-[(2-methyl-5-phenyl-1-(2-pyridyl)pyrrol-3-yl)methyl]piperazine; m.p. 126-128° C., MS: m/z 427 (M+1)

77. 4-(2-methoxyphenyl)-1-[(2-methyl-5-phenyl-1-(2-pyridyl)pyrrol-3-yl)methyl]piperazine; m.p. 92-94° C., MS: m/z 439 (M+1)

78. 4-(3-trifluoromethylphenyl)-1-[(2-methyl-5-phenyl-1-(2-pyridyl)pyrrol-3-yl)methyl]piperazine; m.p. 106-108° C., MS: m/z 477 (M+1)

79. 1-[(2-methyl-5-phenyl-1-(2-pyridyl)pyrrol-3-yl)methyl]-4-(2-pyridyl)piperazine; m.p. 128-130° C., MS: m/z 410 (M+1)

80. 5-({4-[(2-methyl-5-phenyl-1-(2-pyridyl)pyrrol-3-yl)methyl]piperazinyl}methyl)-2H-benzo[d]1,3-dioxolane; thick oil, MS: m/z 467 (M+1)

81. 4-(4-fluorophenyl)-1-[(5-methyl-2-phenyl-1-(2-pyridyl)pyrrol-3-yl)methyl]piperazine; thick oil, MS: m/z 427 (M+1)

82. 4-(2-methoxyphenyl)-1-[(5-methyl-2-phenyl-1-(2-pyridyl)pyrrol-3-yl)methyl]piperazine; m.p. 120-122° C., MS: m/z 439 (M+1)

83. 4-(3-trifluoromethylphenyl)-1-[(5-methyl-2-phenyl-1-(2-pyridyl)pyrrol-3-yl)methyl]piperazine; thick oil, MS: m/z 477 (M+1)

84. 1-[(5-methyl-2-phenyl-1-(2-pyridyl)pyrrol-3-yl)methyl]-4-(2-pyridyl)piperazine; thick oil, MS: m/z 410 (M+1)

85. 5-({4-[(5-methyl-2-phenyl-1-(2-pyridyl)pyrrol-3-yl)methyl]piperazinyl}methyl)-2H-benzo[d]1,3-dioxolane; thick oil, MS: m/z 467 (M+1)

87. 4-[(2-methyl-1,5-diphenylpyrrol-3-yl)methyl]-1,4-thiazaperhydroin-1-one; m.p. 135-137° C., MS: m/z 365 (M+1)

88. 4-[(2-methyl-1,5-diphenylpyrrol-3-yl)methyl]-1,4-thiazaperhydroin-1,1-dione; m.p. 140-142° C., MS: m/z 381 (M+1)

89. N-[5-(4-chlorophenyl)-2-methyl-3-(1,4-thiazaperhydroin-4-ylmethyl)pyrrolyl]-4-pyridylcarboxamide; m.p. 220-222° C., MS: m/z 427 (M+1)
90. 2-[3-(hydroxymethyl)-5-methyl-2-phenyl-4-(1,4-thiazaperhydroin-4-ylmethyl)pyrrolyl]butan-1-ol; m.p. 102-104° C., MS: m/z 375 (M+1)
91. 2-[2-methyl-5-phenyl-3-(1,4-thiazaperhydroin-4-ylmethyl)pyrrolyl]butan-1-ol; m.p. 90-92° C., MS: m/z 345 (M+1)

Microbiology:

Pharmacological Testing

The ability of the compounds of the invention to display antimycobacterial activity can be assessed by growth inhibition assays BACTEC 460 TB System and in vitro agar dilution method as shown in the examples given below.

In vitro growth inhibition and agar dilution assay to determine the minimum inhibitory concentration (MIC) described below indicated that compound of formula (I) of present invention possesses significantly lower MIC values against strains of *M. tuberculosis, M. avium, M. fortiutum*, and *M. kansasii*. The compound (I) of the present invention also inhibits the growth of drug resistant strains of *M. tuberculosis*. Further, the examples given below describe a method to treat experimental tuberculosis in mice. The compounds of the present invention induced better protection at lower doses in comparison to known drugs such as Isoniazid. The compounds can be orally administered in pharmaceutical compositions.

In Vitro Growth Inhibition Assay

The ability of the compounds of present invention to inhibit the growth of *Mycobacterium* species was determined by the BACTEC 460 TB system. The reference strain *M. tuberculosis* $H_{37}Rv$ ATCC 27294 was grown in Middlebrook 7H9 broth containing 10% ADC supplement at 37° C. on a rotary shaker at 150 rpm for 7 days. The turbidity of the culture was adjusted to 1.0 Mc farland. The Middlebrook 7H12B medium vials were seeded with 0.1 ml of the 1.0 Mc farland adjusted *M. tuberculosis* culture. In the control vials 0.1 ml of the culture was added after 100 fold dilution of the initial inoculum. Stock solution of 1 mg/ml of each compound was prepared in DMSO in separate sterile tubes. The compounds were further diluted to concentration of 25 µg/100 □l. 0.1 ml was than added to the 7H12B vial containing mycobacterial culture so that final concentration of the compound is 6.25 µg/ml. The cap in all the vials were cleaned with isopropyl alcohol and kept in racks. The vials were then incubated at 37° C. without shaking. Test vials was read daily on the BACTEC system till the GI of the control vial reached >30. Once the GI in the control reached 30 $\Delta GI$ ($GI=GI_{(n)}-GI_{(n-1)}$) was determined for all test and control vials. If $\Delta GI$ of test vial is less than that of the control vial the culture was sensitive to the test compound.

Table-I gives the in vitro activity observed for the compound of formula (I) against sensitive and resistant strains of *M. tuberculosis*.

TABLE I

| Sr No. | Compound No. | Growth inhibition of *M. tuberculosis* 27294 | MIC (µg/ml) against *M. tuberculosis* 27294 | Clinical isolates Sensitive | Clinical isolates Resistant |
|---|---|---|---|---|---|
| 01 | 1 | + | 0.5 | 0.5-2.0 | 2.0-4.0 |
| 02 | 89 | + | 1.0 | 2.0-8.0 | 4.0-8.0 |
| 03 | 6 | − | ND | | |
| 04 | 2 | + | 0.25 | 0.125-0.25 | 0.25-1.0 |
| 05 | 4 | + | 0.5 | 0.25-1.0 | 0.5-4.0 |
| 06 | 7 | + | 4.0 | 1.0-4.0 | 2.0-4.0 |
| 07 | 8 | + | 1.0 | 0.5-1.0 | 1.0-4.0 |
| 08 | 10 | + | 1.0 | 1.0-2.0 | 1.0-4.0 |
| 09 | 3 | + | 0.125 | 0.125-0.25 | 0.25-0.5 |
| 10 | 9 | − | ND | | |
| 11 | 5 | + | 0.25 | 0.5-1.0 | 0.5-2.0 |
| 12 | 21 | + | 0.5 | 0.5-1.0 | 1.0-4.0 |
| 13 | 87 | + | 8.0 | 8.0-16.0 | 8.0->16.0 |
| 14 | 88 | + | 0.5 | 1.0-4.0 | 2.0-8.0 |
| 15 | 14 | + | 4.0 | 4.0-8.0 | 4.0-8.0 |
| 16 | 90 | − | >16.0 | >16.0 | >16.0 |
| 17 | 91 | + | 4.0 | 4.0-8.0 | 8.0->16.0 |
| 18 | 13 | + | 0.5 | 0.5-2.0 | 1.0-2.0 |
| 19 | 22 | + | 2.0 | 2.0-4.0 | 2.0-4..0 |
| 20 | 11 | + | 1.0 | 0.5-1.0 | 0.5-2.0 |
| 21 | 23 | + | 0.25 | 0.25-1.0 | 0.25-1.0 |
| 22 | 12 | + | 0.25 | 0.25-0.5 | 0.5-1.0 |
| 23 | 46 | + | 2.0 | 2.0-4.0 | 4.0-16.0 |
| 24 | 48 | + | >16.0 | >16.0 | >16.0 |
| 25 | 47 | + | 0.25 | 0.25-1.0 | 1.0-4.0 |
| 26 | 44 | + | 1.0 | 1.0-2.0 | 2.0-4.0 |
| 27 | 45 | + | 0.5 | 0.5-2.0 | 4.0->16.0 |
| 28 | 50 | + | 2.0 | 2.0-4.0 | 4.0-16.0 |
| 29 | 24 | + | 8.0 | 4.0->16.0 | 4.0->16.0 |
| 30 | 17 | + | 2.0 | 2.0-4.0 | 4.0-8.0 |
| 31 | 18 | − | ND | | |
| 32 | 19 | − | 16.0 | 8.0->16.0 | >16.0 |
| 33 | 20 | + | 2.0 | 1.0-4.0 | 4.0-8.0 |
| 34 | 16 | + | 2.0 | 2.0-4.0 | 4.0-16.0 |
| 35 | 15 | + | 0.5 | 0.5-1.0 | 4.0-8.0 |
| 36 | 60 | + | 4.0 | 2.0-8.0 | 4.0-16.0 |

TABLE I-continued

| | | Growth inhibition | MIC (µg/ml) against | | |
| | | | M. tuberculosis | Clinical isolates | |
| Sr No. | Compound No. | of M. tuberculosis 27294 | 27294 | Sensitive | Resistant |
|---|---|---|---|---|---|
| 37 | 62 | + | >16.0 | >16.0 | >16.0 |
| 38 | 25 | + | 2.0 | 2.0-4.0 | 4.0 |
| 39 | 32 | − | >16.0 | >16.0 | >16.0 |
| 40 | 26 | + | 1.0 | 2.0 | 4.0-16.0 |
| 41 | 33 | + | 2.0 | 2.0-8.0 | 4.0-8.0 |
| 42 | 27 | + | 2.0 | 1.0-4.0 | 8.0 |
| 43 | 36 | + | 0.5 | 0.5-1.0 | 1.0-4.0 |
| 44 | 30 | + | 2.0 | 2.0-4.0 | 4.0-16.0 |
| 45 | 34 | + | 16.0 | 16.0-16.0 | >16.0 |
| 46 | 28 | − | 2.0 | 1.0-4.0 | 4.0-16.0 |
| 47 | 35 | + | >16.0 | >16.0 | >16.0 |
| 48 | 29 | + | >16.0 | >16.0 | >16.0 |
| 49 | 41 | − | >16.0 | >16.0 | >16.0 |
| 50 | 37 | − | 16.0 | 8-16.0 | 16->16.0 |
| 51 | 43 | − | >16.0 | >16.0 | >16.0 |
| 52 | 39 | + | 4.0 | 4.0-8.0 | 8.0->16.0 |
| 53 | 42 | + | 8.0 | 8.0 | 8.0->16.0 |
| 54 | 38 | − | >16.0 | >16.0 | >16.0 |
| 55 | 55 | − | >16.0 | >16.0 | >16.0 |
| 56 | 51 | − | >16.0 | >16.0 | >16.0 |
| 57 | 56 | + | 8.0 | 8.0 | 8.0-16.0 |
| 58 | 52 | + | 8.0 | 8.0 | 8.0-16.0 |
| 59 | 57 | + | >16.0 | >16.0 | >16.0 |
| 60 | 53 | − | >16.0 | >16.0 | >16.0 |
| 61 | 58 | + | 8.0 | 8.0 | 8.0-16.0 |
| 62 | 54 | + | 2.0 | 4.0 | 4.0 |
| 63 | 64 | − | >16.0 | >16.0 | >16.0 |
| 64 | 61 | + | 4.0 | 4.0-8.0 | 4.0-8.0 |
| 65 | 59 | − | >16.0 | >16.0 | >16.0 |
| 66 | 63 | + | 8.0 | 4.0-8.0 | 4.0-16.0 |
| 67 | Isoniazid | + | 0.25 | 0.125-0.25 | 8.0->16.0 |
| 68 | Rifampin | + | 0.25 | 0.25 | 4.0-16.0 |

Table-II gives the MIC values of compound of formula (I) against different species of *Mycobacteria*.

TABLE II

| | | MIC (µg/ml) | | | | |
| | | M. tuberculosis | | | | |
| Sr. No | Compound No. | Sensitive (n = 17) | Resistant (n = 26) | M. aviumintracellulare complex (n = 13) | M. fortuitum (n = 8) | M. kansasii (n = 2) |
|---|---|---|---|---|---|---|
| 1 | 2 | 0.125-0.25 | 0.25-1.0 | 4.0-8.0 | 8.0-16.0 | 8.0 |
| 2 | 3 | 0.125-0.25 | 0.25-0.5 | 4.0-8.0 | 4.0-8.0 | 4.0 |
| 3 | 5 | 0.5-1.0 | 1.0-2.0 | 4.0-8.0 | 8.0-16.0 | 8.0 |
| 4 | Isoniazid | 0.25 | 8.0->16.0 | 8.0->16.0 | >16.0 | >16.0 | n: Number of strains tested

In Vitro Agar Dilution Assay:

MIC of compounds against strains of *Mycobacterium* were determined by a reference agar dilution method as per the NCCLS-M24-T2 recommendations. The compounds were dissolved in DMSO and diluted twofold to obtain ten serial dilutions of each compound. Appropriate volume of compounds were incorporated into duplicate plates of Middlebrook 7H10 agar medium supplemented with 10% Middlebrook supplement oleic acid-albumin-dextrose catalase (OADC) enrichment at concentration of 0.03 µg/ml to 16 µg/ml. Test organisms (*Mycobacterium* strains) were grown in Middle brook 7H9 broth containing 0.05% Tween-80 and 10% ADC supplement. After 7 days of incubation at 37° C. the broths were adjusted to the turbidity of 1.0 McFarland standard; the organism were further diluted 10 fold in sterile saline containing 0.10% Tween-80. The resulting mycobacterial suspensions were spotted (3-5 □l/spot) onto drug supplemented 7H10 media plates. The plates were sealed and incubated at 37° C. for 3-4 weeks in upright position. The MIC was recorded as the highest dilution of the drug that completely inhibited the growth of test organisms. Test isolates included 10 clinical isolates that were generally susceptible to common antitubercular agents and 10 strains that were resistant to one or more standard anti tubercular drugs. Appropriate reference strains and control drug was included in each batch of test.

In Vivo Studies

The efficacy of the compounds of present invention was also evaluated in murine model of pulmonary tuberculosis. *Mycobacterium tuberculosis* $H_{37}Rv$ cultures grown in Middle brook 7H9 broth containing 0.05% Tween-80 and 10% ADC supplement at 37° C. for 7 days on a rotary shaker at 150 rpm. For, animal inoculation liquid cultures were declumped by brief sonication and were diluted appropriately in 7H9 broth to obtain a concentration of $1\times10^7$ CFU's/0.2 ml. Four-week-old male outbred Swiss albino mice housed in a pathogen free, biosafety level 3 environments within microisolator cages were used throughout the study. Infections were produced by intravenous inoculation of 0.2 ml of declumped *M. tuberculosis* $H_{37}R_v$ suspension into caudal tail vein. Following infection mice were randomly distributed in different groups of six each.

Treatment for initial study started 1 day after infection. For the treatment, the compound No 3 was dissolved and diluted in 50% polyethylene glycol 400 (PEG-400), Isoniazid was dissolved in sterile water. The drugs were prepared each morning prior to administration. Therapy was given 5 days a week for four weeks. All the agents were administered by gavage and were dosed at 50, 25, 12.5 mg/kg of body weight. Control group of infected but untreated mice were killed at the initiation of therapy (early control) or at the end of the treatment period (late control). Mice were sacrificed by cervical dislocation 3-5 days after the administration of the last dose of drug. Target organs i.e. spleen and right lung were removed aseptically and homogenized in tissue homogenizer. At least 4 serial tenfold dilution of the homogenate was made in 7H9 broth and plated onto selective Middlebrook 7H11 agar plates in duplicate. The colony counts were recorded after incubation at 37° C. for 4 weeks. The viable cell counts were converted to Log10 values. A compound showing 2 log10 reduction in viable counts compared to the early controls was considered significant.

The in vivo activity of compound No. 3 of formula (I) against *M. tuberculosis* $H_{37}R_v$ ATCC 27294[a] infection in Swiss albino mice is summarized in Table-III

TABLE III

| Sr. No. | Drug & Dose[b] (mg/kgday$^{-1}$) or group | Mean Log10 No. of CFU Lung | Mean Log10 No. of CFU Spleen | Mean Log10 no. of reduction[c] Lung | Mean Log10 no. of reduction[c] Spleen |
|---|---|---|---|---|---|
| 1 | Compound No. 3 | | | | |
|   | 50 mg/kg | 1.97 | 1.94 | 2.51 | 2.64 |
|   | 25 mg/kg | 2.13 | 2.07 | 2.35 | 2.29 |
|   | 12.5 mg/kg | 2.63 | 2.6 | 1.85 | 2.03 |
| 2 | Isoniazid | | | | |
|   | 50 mg/kg | 1.95 | 2.12 | 2.53 | 2.51 |
|   | 25 mg/kg | 2.16 | 2.21 | 2.36 | 2.27 |
|   | 12.5 mg/kg | 2.93 | 2.91 | 1.55 | 1.72 |
| 3 | Infected early control | 4.48 | 4.63 | | |
| 4 | Infected late control | 6.68 | 6.67 | | |

[a]inoculation of $10^7$ cfu/mouse
[b]mice were dosed 5 day/week for 4 week. From day 1-28
[c]difference in mean log10 number CFU from that of early controls The in vivo efficacy of Compound No. 12 of formula (I) against *M. tuberculosis* $H_{37}$Rv ATCC 27294[a] infection in mice model treated 14 days post-infection and its comparison with isoniazid is summarized in Table-IV.

TABLE IV

| Sr. No. | Drug & Dose[b] (mg/kgday$^{-1}$) or group | Mean Log10 No. of CFU Lung | Mean Log10 No. of CFU Spleen | Mean Log10 no. of reduction[c] Lung | Mean Log10 no. of reduction[c] Spleen |
|---|---|---|---|---|---|
| 1 | Compound No. 12 | | | | |
|   | 50 mg/kg | 2.74 + 0.36 | 2.78 + 0.32 | 2.85 | 3.17 |
|   | 25 mg/kg | 2.87 + 0.15 | 2.83 + 0.29 | 2.72 | 3.12 |
|   | 12.5 mg/kg | 4.18 + 0.38 | 4.41 + 0.26 | 1.41 | 1.54 |
| 2 | Isoniazid | | | | |
|   | 50 mg/kg | 2.97 + 0.46 | 2.89 + 0.27 | 2.62 | 3.06 |
|   | 25 mg/kg | 3.19 + 0.6 | 3.08 + 0.44 | 2.4 | 2.87 |
|   | 12.5 mg/kg | 4.56 + 0.24 | 4.93 + 0.42 | 1.03 | 1.02 |
| 3 | Infected early control | 5.59 + 0.29 | 5.95 + 0.42 | | |
| 4 | Infected late control | 7.3 + 0.2 | 7.27 + 0.42 | | |

[a]inoculation of $10^7$ cfu/mouse
[b]mice were dosed 5 day/week for 4 week. From day 1-28
[c]difference in mean log10 number CFU from that of early controls The in vivo efficacy of Compound No. 3 of formula (I) against *M. tuberculosis* (Resistant strain)[a] treated 01 day post-infection in mice model and its comparison with isoniazid is summarized in Table-V.

TABLE V

| Sr. No. | Drug & Dose[b] (mg/kgday$^{-1}$) or group | Mean Log10 No. of CFU Lung | Mean Log10 No. of CFU Spleen | Mean Log10 No. of reduction[c] Lung | Mean Log10 No. of reduction[c] Spleen |
|---|---|---|---|---|---|
| 1 | Compound No. 3 | | | | |
|   | 50 mg/kg | 1.99 + 0.3 | 1.97 + 0.4 | 2.48 | 2.66 |
|   | 25 mg/kg | 2.3 + 0.17 | 2.2 + 0.31 | 2.17 | 2.43 |
|   | 12.5 mg/kg | 2.98 + 0.5 | 2.91 + 0.4 | 1.49 | 1.72 |
| 2 | Isoniazid | | | | |
|   | 50 mg/kg | 4.43 + 0.5 | 4.7 + 0.31 | 0.04 | −0.07 |
|   | 25 mg/kg | 5.12 + 0.6 | 5.43 + 0.5 | −0.65 | −0.8 |
|   | 12.5 mg/kg | 5.8 + 0.4 | 5.79 + 0.4 | −1.33 | −1.16 |
| 3 | Infected early control | 4.47 + 0.31 | 4.63 + 0.21 | | |
| 4 | Infected late control | 6.39 + 0.5 | 6.23 + 0.21 | | |

[a]inoculation of $10^7$ cfu/mouse
[b]mice were dosed 5 day/week for 4 week. From day 1-28
[c]difference in mean log10 number CFU from that of early controls The in vivo efficacy of Compound No 12 of formula (I) against *M. tuberculosis* $H_{37}$ Rv ATCC 27294[a] treated 01 day post-infection in mice model and its comparison with isoniazid is summarized in Table-VI.

TABLE VI

| Sr. No. | Drug & Dose[b] (mg/kgday$^{-1}$) or group | Mean Log10 No. of CFU Lung | Mean Log10 No. of CFU Spleen | Mean Log10 No. of reduction[c] Lung | Mean Log10 No. of reduction[c] Spleen |
|---|---|---|---|---|---|
| 1 | Compound No. 12 | | | | |
|   | 50 mg/kg | 1.89 + 0.24 | 1.94 + 0.23 | 2.68 | 2.75 |
|   | 25 mg/kg | 2.1 + 0.24 | 2.13 + 0.28 | 2.47 | 2.56 |
|   | 12.5 mg/kg | 2.34 + 0.18 | 2.26 + 0.21 | 2.23 | 2.43 |

TABLE VI-continued

| Sr. No. | Drug & Dose[b] (mg/kgday[-1]) or group | Mean Log10 No. of CFU | | Mean Log10 No. of reduction[c] | |
|---|---|---|---|---|---|
| | | Lung | Spleen | Lung | Spleen |
| 2 | Isoniazid | | | | |
| | 50 mg/kg | 2.02 + 0.31 | 2.07 + 0.33 | 2.55 | 2.62 |
| | 25 mg/kg | 2.23 + 0.33 | 2.21 + 0.44 | 2.34 | 2.48 |
| | 12.5 mg/kg | 2.89 + 0.27 | 2.91 + 0.42 | 1.68 | 1.78 |
| 3 | Infected early control | 4.57 + 0.2 | 4.69 + 0.21 | — | |
| 4 | Infected late control | 6.39 + 0.5 | 6.2 + 0.32 | — | |

[a]inoculation of $10^7$ cfu/mouse
[b]mice were dosed 5 day/week for 4 week. From day 1-28
[c]difference in mean log10 number CFU from that of early controls While, the present invention has been described in terms of its specific embodiments, certain modifications and equivalents will be apparent to those skilled in the art and are intended to be included within the scope of the present invention.

Acute Toxicity Study in Mice

Compound No. 3 of formula (I) was administered, as a single oral dose, in Swiss albino mice. Two dose levels of 500 and 2000 mg/kg were employed. The mice were observed for 14 days. No clinical symptom or mortality was observed. The mice were sacrificed on day 15 but no pathological changes were seen in any organ. Therefore $LD_0$ was >2000 mg/kg by oral route in mice. Reported $LD_{50}$ of INH (Isoniazid) is 139 mg/kg in mice by oral route. Similarly in compound No. 12 of Formula I, $LD_0$ was >500 mg/kg by oral route in mice.

The invention claimed is:

1. A compound of formula (I), and pharmaceutically acceptable salts thereof

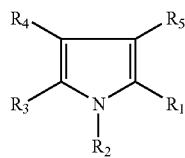

wherein:
 $R_1$ is $C_1$-$C_4$ alkyl, $C_1$-$C_4$ alkoxy, $C_1$-$C_4$ thioalkoxy, trifluoroalkyl, trifluoroalkoxy or, hydroxyalkyl;
 $R_2$ is pyridine or
 $NHCOR_6$, wherein $R_6$ is pyridyl;
 $R_3$ is phenyl or substituted phenyl;
 $R_4$ and $R_5$ are H or —$(CH_2)_n$—$R_7$;
  when one of $R_4$ and $R_5$ is H, the other is —$(CH_2)_n$—$R_7$, wherein n=1-3 and $R_7$ is selected from

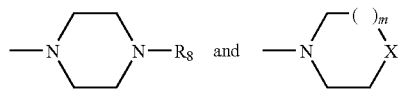

wherein $R_8$ is phenyl which is unsubstituted or substituted with 1-2 substituents each independently selected from the group consisting of halogen, $C_1$-$C_4$ alkyl, $C_1$-$C_4$ alkoxy, $C_1$-$C_4$ thioalkoxy, nitro, amino, haloalkyl, haloalkoxy; benzyl or benzyl substituted with 3,4-methylenedioxy; heteroaryl; heteroaroyl; diphenylmethyl;
 m=0-2; and
 X=—$NCH_3$, $CH_2$, S, SO, or $SO_2$;
further wherein: when $R_2$ is pyridine, $R_7$ is:

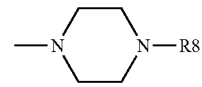

wherein $R_8$ is as defined above.

2. The compound of claim 1 wherein the compound is:
N-(3-{[4-(4-fluorophenyl)piperazinyl]methyl}-2-methyl-5-phenylpyrrolyl)-4-pyridylcarboxamide,
N-(3-{[4-(3-trifluoromethylphenyl)piperazinyl]methyl}-2-methyl-5-phenyl-pyrrolyl)-4-pyridylcarboxamide,
N-(3-{[4-(2-methoxyphenyl)piperazinyl]methyl}-2-methyl-5-phenylpyrrolyl)-4-pyridylcarboxamide,
N-(3-{[4-(2-pyridyl)piperazinyl]methyl}-2-methyl-5-phenylpyrrolyl)-4-pyridylcarboxamide,
N-(2-methyl-5-phenyl-3-{[4-benzylpiperazinyl]methyl}pyrrolyl)-4-pyridylcarboxamide,
N-{2-methyl-3-[(4-methylpiperazinyl)methyl]-5-phenylpyrrolyl)-4-pyridylcarboxamide,
N-(3-{[4-(2H-benzo[d] 1,3-dioxolen-5-ylmethyl)piperazinyl]methyl}-2-methyl-S-phenylpyrrolyl)-4-pyridylcarboxamide,
N-[2-methyl-5-phenyl-3-(piperidinylmethyl)pyrrolyl]-4-pyridylcarboxamide,
N-[2-methyl-5-phenyl-3-(pyrrolidinylmethyl)pyrrolyl]-4-pyridylcarboxamide,
N-[2-methyl-5-phenyl-3-(1,4-thiazaperhydroin-4-ylmethyl)pyrrolyl]-4-pyridylcarboxamide,
N-(3-{[4-(4-fluorophenyl)piperazinyl]methyl}-5-methyl-2-phenylpyrrolyl)-4-pyridylcarboxamide,
N-(3-{[4-(3-trifluoromethylphenyl)piperazinyl]methyl}-5-methyl-2-phenyl pyrrolyl)-4-pyridylcarboxamide,
N-(3-{[4-(2H-benzo[3,4-d]1,3-dioxolan-5-ylmethyl)piperazinyl]methyl}-5-methyl-2-phenylpyrrolyl)-4-pyridylcarboxamide,
N-(5-(4-chlorophenyl)-3-{[4-(4-fluorophenyl)piperazinyl]methyl}-2-methylpyrrolyl)-4-pyridylcarboxamide,
N-(5-(4-chlorophenyl)-3-{[4-(2-methoxyphenyl)piperazinyl]methyl}-2-methylpyrrolyl)-4-pyridylcarboxamide,
N-(5-(4-chlorophenyl)-3-{[4-(3-trifluoromethylphenyl)piperazinyl]methyl}-2-methylpyrrolyl)-4-pyridylcarboxamide,
N-(5-(4-chlorophenyl)-3-{[4-(2-pyridyl)piperazinyl]methyl}-2-methyl-pyrrolyl)-4-pyridylcarboxamide,
N-(3-{[4-(2H-benzo[d] 1,3-dioxolan-5-ylmethyl)piperazinyl]methyl}-5-(4-chlorophenyl)-2-methylpyrrolyl)-4-pyridylcarboxamide,
N-(2-(4-chlorophenyl)-3-{[4-(4-fluorophenyl)piperazinyl]methyl}-5-methyl-pyrrolyl)-4-pyridylcarboxamide,
N-(2-(4-chlorophenyl)-3-{[4-(2-methoxyphenyl)piperazinyl]methyl}-5-methylpyrrolyl)-4-pyridylcarboxamide,
N-(2-(4-chlorophenyl)-3-{[4-(3-trifluoromethylphenyl)piperazinyl]methyl}-5-methylpyrrolyl)-4-pyridylcarboxamide, N-(2-(4-chlorophenyl)-3-{[4-(2-pyridyl)piperazinyl]methyl}-5-methylpyrrolyl)-4-pyridylcarboxamide,
N-(3-{[4-(2H-benzo[3,4-d]1,3-dioxolan-5-ylmethyl)piperazinyl]methyl}-2-(4-chloro phenyl)-5-methylpyrrolyl)-4-pyridylcarboxamide,
4-(4-fluorophenyl)-1-[(2-methyl-5-phenyl-1-(2-pyridyl)pyrrol-3-yl)methyl]-piperazine,
4-(2-methoxyphenyl)-1-[(2-methyl-5-phenyl-1-(2-pyridyl)pyrrol-3-yl)methyl]-piperazine,
4-(3-trifluoromethylphenyl)-1-[(2-methyl-5-phenyl-1-(2-pyridyl)pyrrol-3-yl)methyl]piperazine,
4-(2-pyridyl)-1-[2-methyl-5-phenyl-1-(2-pyridyl)pyrrol-3-yl)methyl]-piperazine,
5-({4-[(2-methyl-5-phenyl-1-(2-pyridyl)pyrrol-3-yl)methyl]piperazinyl}methyl)-2H-benzo[d]1,3-dioxolane,
4-(4-fluorophenyl)-1-[(5-methyl-2-phenyl-1-(2-pyridyl)pyrrol-3-yl)methyl]piperazine,
4-(2-methoxyphenyl)-1-[(5-methyl-2-phenyl-1-(2-pyridyl)pyrrol-3-yl)methyl]piperazine,
4-(3-trifluoromethylphenyl)-1-[(5-methyl-2-phenyl-1-(2-pyridyl)pyrrol-3-yl)methyl]piperazine,
1-[(5-methyl-2-phenyl-1-(2-pyridyl)pyrrol-3-yl)methyl]-4-(2-pyridyl)-piperazine,
5-({4-[(5-methyl-2-phenyl-1-(2-pyridyl)pyrrol-3-yl)methyl]piperazinyl}methyl)-2H-benzo[d]1,3-dioxolane,
N-[5-(4-chlorophenyl)-2-methyl-3-(1,4-thiazaperhydroin-4-ylmethyl)pyrrolyl]-4-pyridyl carboxamide, or pharmaceutically acceptable salt thereof.

3. A pharmaceutical composition comprising a pharmaceutically acceptable carrier and a compound of formula (I)

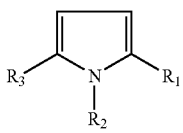

(V)

wherein:
R$_1$ is C$_1$-C$_4$ alkyl, C$_1$-C$_4$ alkoxy, C$_1$-C$_4$ thioalkoxy, trifluoroalkyl, trifluoroalkoxy or, hydroxyalkyl;
R$_2$ is pyridine or NHCOR$_6$, wherein R$_6$ is pyridine;
R$_3$ is phenyl or substituted phenyl;
R$_4$ and R$_5$ are H or —(CH$_2$)$_n$—R$_7$;
when one of R$_4$ and R$_5$ is H, the other is —(CH$_2$)$_n$—R$_7$, wherein n=1-3 and R$_7$ is selected from

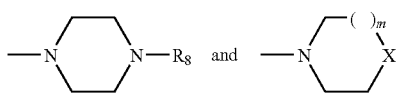

wherein R$_8$ is phenyl which is unsubstituted or substituted with 1-2 substituents each independently selected from the group consisting of halogen, C$_1$-C$_4$ alkyl, C$_1$-C$_4$ alkoxy, C$_1$-C$_4$ thioalkoxy, nitro, amino, haloalkyl, haloalkoxy; benzyl or benzyl substituted with 3,4-methylenedioxy; heteroaryl; heteroaroyl; diphenylmethyl;
m=0-2; and
X=—NCH$_3$, CH$_2$, S, SO, or SO$_2$;

further wherein: when R$_2$ is pyridine, R$_7$ is:

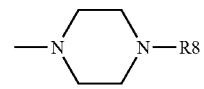

wherein R$_8$ is as defined above; or
a pharmaceutically acceptable salt thereof.

4. The composition of claim 3 comprising a solid or liquid preparation.

5. The composition of claim 3, the composition being for oral or parenteral administration.

6. A method of inhibiting the growth of a microbial cell comprising contacting the microbial cell with a compound of formula (I):

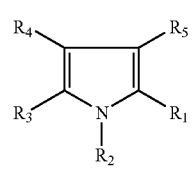

(I)

wherein:
R$_1$ is C$_1$-C$_4$ alkyl, C$_1$-C$_4$ alkoxy, C$_1$-C$_4$ thioalkoxy, trifluoroalkyl, trifluoroalkoxy or, hydroxyalkyl;
R$_2$ is pyridine or NHCOR$_6$, wherein R$_6$ is pyridine;
R$_3$ is phenyl or substituted phenyl;
R$_4$ and R$_5$ are H or —(CH$_2$)$_n$—R$_7$;
when one of R$_4$ and R$_5$ is H, the other is —(CH$_2$)$_n$—R$_7$, wherein n=1-3 and R$_7$ is selected from

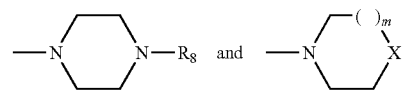

wherein R$_8$ is phenyl which is unsubstituted or substituted with 1-2 substituents each independently selected from the group consisting of halogen, C$_1$-C$_4$ alkyl, C$_1$-C$_4$ alkoxy, C$_1$-C$_4$ thioalkoxy, nitro, amino, haloalkyl, haloalkoxy; benzyl or benzyl substituted with 3,4-methylenedioxy; heteroaryl; heteroaroyl; diphenylmethyl;
m=0-2; and
X=—NCH$_3$, CH$_2$, S, SO, or SO$_2$;
further wherein: when R$_2$ is pyridine, R$_7$ is:

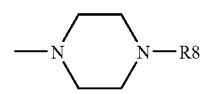

wherein R$_8$ is as defined above; or
a pharmaceutically acceptable salt thereof.

7. The method of claim 6, wherein the microbial cell is *Mycobacterium tuberculosis*, drug resistant *M. tuberculosis, M. aviumintracellulare* complex, *M. fortuitum, M. kansasii*, or mixture thereof.

8. A method of reducing the population of mycobacteria in a mammal, comprising administering to the mammal an antimycobacterial effective amount of a compound of formula (I):

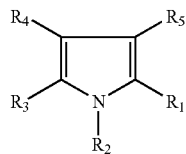
(I)

wherein:
R$_1$ is C$_1$-C$_4$ alkyl, C$_1$-C$_4$ alkoxy, C$_1$-C$_4$ thioalkoxy, trifluoroalkyl, trifluoroalkoxy or, hydroxyalkyl;
R$_2$ is pyridine or NHCOR$_6$, wherein R$_6$ is pyridine;
R$_3$ is phenyl or substituted phenyl;
R$_4$ and R$_5$ are H or 4-CH$_2$)$_n$—R$_7$;
when one of R$_4$ and R$_5$ is H, the other is —(CH$_2$)$_n$—R$_7$, wherein n=1-3 and R$_7$ is selected from

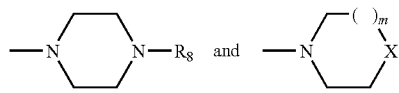

wherein R$_8$ is phenyl which is unsubstituted or substituted with 1-2 substituents each independently selected from the group consisting of halogen, C$_1$-C$_4$ alkyl, C$_1$-C$_4$ alkoxy, C$_1$-C$_4$ thioalkoxy, nitro, amino, haloalkyl, haloalkoxy; benzyl or benzyl substituted with 3,4-methylenedioxy; heteroaryl; heteroaroyl; diphenylmethyl;
m=0-2; and
X=—NCH$_3$, CH$_2$, S, SO, or SO$_2$;
further wherein: when R$_2$ is pyridine, R$_7$ is:

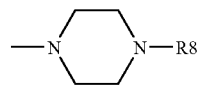

wherein R$_8$ is as defined above; or
a pharmaceutically acceptable salt thereof.

9. The method of claim 7, wherein the mammal suffers from tuberculosis.

10. A process for preparing a compound of formula (I) comprising

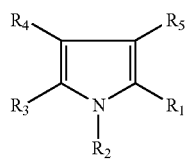
(I)

reacting a compound of formula (V)

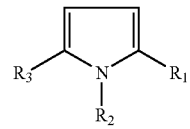
(V)

wherein:
R$_1$ is C$_1$-C$_4$ alkyl, C$_1$-C$_4$ alkoxy, C$_1$-C$_4$ thioalkoxy, trifluoroalkyl, trifluoroalkoxy or, hydroxyalkyl,
R$_2$ is pyridine or NHCOR$_6$, wherein R$_6$ is pyridyl; and
R$_3$ is phenyl or substituted phenyl;
with an amine of formula R$_7$H, wherein R$_7$ is

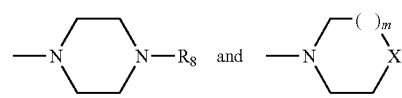

wherein R$_8$ is phenyl which is unsubstituted or substituted with 1-2 substituents each independently selected from the group consisting of halogen, C$_1$-C$_4$ alkyl, C$_1$-C$_4$ alkoxy, C$_1$-C$_4$ thioalkoxy, nitro, amino, haloalkyl, haloalkoxy; benzyl or benzyl substituted with 3,4-methylenedioxy; heteroaryl; heteroaroyl; diphenylmethyl,
m=0-2 and
X=—NCH$_3$, CH$_2$, S, SO, or SO$_2$;
such that in the compound of formula I thus produced:
when one of R$_4$ and R$_5$ is H, the other is —(CH$_2$)$_n$—R$_7$; and
when R$_2$ is pyridine, R$_7$ is:

wherein R$_8$ is as defined above;
in an aprotic polar solvent in presence of acetic acid.

11. The process of claim 10, wherein the compound of formula (V) is prepared by reacting a compound of formula (IV)

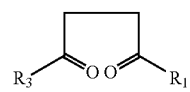
(IV)

wherein: R$_1$ is C$_1$-C$_4$ alkyl, C$_1$-C$_4$ alkoxy, C$_1$-C$_4$ thioalkoxy, trifluoroalkyl, trifluoroalkoxy or, hydroxyalkyl; and R$_3$ is phenyl or substituted phenyl;
with an amine of formula R$_2$NH$_2$, wherein R$_2$ is pyridine or HCOR$_6$, wherein R$_6$ is aryl, unsubstituted or substituted heteroaryl, unsubstituted or substituted heterocyclyl;
in a suitable organic solvent, wherein the reaction is effected by removal of water molecule in presence of molecular sieves or para-toluenesulfonic acid or mixtures thereof.

12. A process according to claim 11, wherein the compound of formula (IV) is prepared by reacting compound of formula (II)

$$R_3\text{—}H \quad (II)$$

wherein $R_3$ is selected from the group consisting of phenyl, chlorobenzene, bromobenzene, fluorobenzene, 1,2-dichlorobenzene, 1,2-dibromobenzene, 1,2-difluorobenzene, 1,3-dichlorobenzene, 1,3-dibromobenzene, 1,3-difluorobenzene, 1,4-difluorobenzene, 1,4-dibromobenzene, 1,4-difluorobenzene, methylbenzene, ethylbenzene, o-xylene, m-xylene, p-xylene, 2-ethyl toluene. 3-ethyl toluene, 4-ethyl toluene, propyl benzene, cumene, butyl benzene, sec-butyl benzene, iso-butyl benzene, tert-butyl benzene, o-cymene, m-cymene, p-cymene, 1,2-diethyl benzene, 1,3-diethyl benzene, 1,4-diethylbenzene, 1,3-di-tert-butyl benzene, 1,4-di-tert-butyl benzene, 4-tert butyl toluene, anisole, 2-methyl anisole, 3-methyl anisole, 4-methyl anisole, 1,2-benzenedimethanol, 1,3-benzenedimethanol, 1,4-benzenedimethanol, 1,2-dimethoxybenzene, 2-ethoxyanisole, 3,5-diethoxytoluene, benzylmercaptan, phenethylmercaptan, 1,2-benzenedimethanethiol, 1,3-benzenedimethanethiol, 1,4-benzenedimethanethiol, benzyl chloride, benzyl bromide, trifluoromethoxybenzene, and trifluoroethoxybenzene;

with a compound of formula (III)

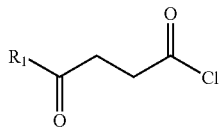

wherein $R_1$ is $C_1$-$C_4$ alkyl $C_1$-$C_4$ alkoxy, $C_1$-$C_4$ thioalkoxy, trifluoroalkyl, trifluoroalkoxy or, hydroxyalkyl; in presence of anhydrous aluminum chloride.

13. The process of claim 11, wherein the compound of formula (IV) is prepared by reacting compound of formula (VI)

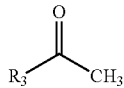

wherein $R_3$ is phenyl or substituted phenyl, with a compound of formula (VII)

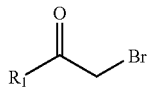

wherein $R_1$ is $C_1$-$C_4$ alkyl, $C_1$-$C_4$ alkoxy, $C_1$-$C_4$ thioalkoxy, trifluoroalkyl, trifluoroalkoxy or, hydroxyalkyl; in presence of anhydrous zinc chloride, triethyl amine and tert butanol in benzene.

14. The method of claim 6, wherein the microbial cell is drug resistant.

15. The method of claim 6, wherein the compound of formula (I) is provided with a pharmaceutically acceptable carrier.

16. The method of claim 6, wherein the compound of formula (I) is provided with a pharmaceutically acceptable carrier.

17. A compound of formula (I) according to claim 1 wherein the compound is:
- 5-[(4-{[1,5-bis(4-chlorophenyl)-2-methylpyrrol-3-yl] methyl}piperazinyl)methyl]-2H-benzo[d] 1,3-dioxolane;
- N-(3-{[4-(2H-benzo[d] 1,3-dioxolen-5-ylmethyl)piperazinyl]methyl}}-2-methyl-5-phenylpyrrolyl)-4-pyridylcarboxamide;
- N-(3-{[4-(2H-benzo[3,4-d]1,3-dioxolen-5-ylmethyl)piperazinyl]methyl}}-5-methyl-2-phenylpyrrolyl)-4-pyridylcarboxamide;
- N-(3-{[4-(2H-benzo[d] 1,3-dioxolen-5-ylmethyl)piperazinyl]methyl}}-2-methyl-5-phenylpyrrolyl)pyrazin-2-ylcarboxamide;
- N-(3-{[4-(2H-benzo[3,4-d]1,3-dioxolan-5-ylmethyl)piperazinyl]methyl}}-5-methyl-2-phenylpyrrolyl)pyrazin-2-ylcarboxamide;
- 5-[(4-{[1-(2,4-difluorophenyl)-5-(4-chlorophenyl)-2-methylpyrrol-3-yl]methyl}piperazinyl)methyl]-2H-benzo [d] 1,3-dioxolene;
- 5-[(4-{[5-(4-chlorophenyl)-2-methyl-1-naphthylpyrrol-3-yl]methyl}-piperazinyl)methyl]2H-benzo[d] 1,3-dioxolene;
- N-(3-{[4-(2H-benzo[d] 1,3-dioxolen-5-ylmethyl)piperazinyl]methyl}-5-(4-chlorophenyl)-2-methylpyrrolyl)-4-pyridylcarboxamide;
- N-(3-{[4-(2H-benzo[3,4-d]1,3-dioxolan-5-ylmethyl)piperazinyl]methyl}-2-(4-chloro phenyl)-5-methylpyrrolyl)-4-pyridyl carboxamide;
- 5-({4-[(2-methyl-5-phenyl-1-(2-pyridyl)pyrrol-3-ylmethyl]piperazinyl}methyl)-2H-benzo[d] 1,3-dioxolane;
- 5-({4-[(5-methyl-2-phenyl-1-(2-pyridyl)pyrrol-3-yl)methyl]piperazinyl}-methyl)-2H-benzo[d] 1,3-dioxolane; or pharmaceutically acceptable salts thereof.

18. The compound of claim 1, wherein when $R_3$ is substituted phenyl the substituted phenyl is selected from the group consisting of chlorobenzene, bromobenzene, fluorobenzene, 1,2-dichlorobenzene, 1,2-dibromobenzene, 1,2-difluorobenzene, 1,3-dichlorobenzene, 1,3-dibromobenzene, 1,3-difluorobenzene, 1,4-difluorobenzene, 1,4-dibromobenzene, 1,4-difluorobenzene, methylbenzene, ethylbenzene, o-xylene, m-xylene, p-xylene, 2-ethyl toluene, 3-ethyl toluene, 4-ethyl toluene, propyl benzene, cumene, butyl benzene, sec-butyl benzene, iso-butyl benzene, tert-butyl benzene, o-cymene, m-cymene, p-cymene, 1,2-diethyl benzene, 1,3-diethyl benzene, 1,4-diethylbenzene, 1,3-di-tert-butyl benzene, 1,4-di-tert-butyl benzene, 4-tert butyl toluene, anisole, 2-methyl anisole, 3-methyl anisole, 4-methyl anisole, 1,2-benzenedimethanol, 1,3-benzenedimethanol, 1,4-benzenedimethanol, 1,2-dimethoxybenzene, 2-ethoxyanisole, 3,5-diethoxytoluene, benzylmercaptan, phenethylmercaptan, 1,2-benzenedimethanethiol, 1,3-benzenedimethanethiol, 1,4-benzenedimethanethiol, nitrobenzene, 1,2-dinitrobenzene, 1,3-dinitrobenzene, 1,4-dinitrobenzene, benzyl chloride, benzyl bromide, trifluoromethoxybenzene, and trifluoroethoxybenzene.

19. The composition of claim 3, wherein when $R_3$ is substituted phenyl the substituted phenyl is selected from the group consisting of chlorobenzene, bromobenzene, fluorobenzene, 1,2-dichlorobenzene, 1,2-dibromobenzene, 1,2- difluorobenzene, 1,3-dichlorobenzene, 1,3-dibromobenzene, 1,3-difluorobenzene, 1,4-difluorobenzene, 1,4-dibromobenzene, 1,4-difluorobenzene, methylbenzene, ethylbenzene, o-xylene, m-xylene, p-xylene, 2-ethyl toluene, 3-ethyl toluene, 4-ethyl toluene, propyl benzene, cumene, butyl benzene, sec-butyl benzene, iso-butyl benzene, tert-butyl benzene, o-cymene, m-cymene, p-cymene, 1,2-diethyl benzene, 1,3-diethyl benzene, 1,4-diethylbenzene, 1,3-di-tert-butyl benzene, 1,4-di-tert-butyl benzene, 4-tert butyl toluene, anisole, 2-methyl anisole, 3-methyl anisole, 4-methyl anisole, 1,2-benzenedimethanol, 1,3-benzenedimethanol, 1,4-benzenedimethanol, 1,2-dimethoxybenzene, 2-ethoxyanisole, 3,5-diethoxytoluene, benzylmercaptan, phenethylmercaptan, 1,2-benzenedimethanethiol, 1,3-benzenedimethanethiol, 1,4-benzenedimethanethiol, nitrobenzene, 1,2-dinitrobenzene, 1,3-dinitrobenzene, 1,4-dinitrobenzene, benzyl chloride, benzyl bromide, trifluoromethoxybenzene, and trifluoroethoxybenzene.

20. The method of claim 6, wherein when $R_3$ is substituted phenyl the substituted phenyl is selected from the group consisting of chlorobenzene, bromobenzene, fluorobenzene, 1,2-dichlorobenzene, 1,2-dibromobenzene, 1,2-difluorobenzene, 1,3-dichlorobenzene, 1,3-dibromobenzene, 1,3-difluorobenzene, 1,4-difluorobenzene, 1,4-dibromobenzene, 1,4-difluorobenzene, methylbenzene, ethylbenzene, o-xylene, m-xylene, p-xylene, 2-ethyl toluene, 3-ethyl toluene, 4-ethyl toluene, propyl benzene, cumene, butyl benzene, sec-butyl benzene, iso-butyl benzene, tert-butyl benzene, o-cymene, m-cymene, p-cymene, 1,2-diethyl benzene, 1,3-diethyl benzene, 1,4-diethylbenzene, 1,3-di-tert-butyl benzene, 1,4-di-tert-butyl benzene, 4-tert butyl toluene, anisole, 2-methyl anisole, 3-methyl anisole, 4-methyl anisole, 1,2-benzenedimethanol, 1,3-benzenedimethanol, 1,4-benzenedimethanol, 1,2-dimethoxybenzene, 2-ethoxyanisole, 3,5-diethoxytoluene, benzylmercaptan, phenethylmercaptan, 1,2-benzenedimethanethiol, 1,3-benzenedimethanethiol, 1,4-benzenedimethanethiol, nitrobenzene, 1,2-dinitrobenzene, 1,3-dinitrobenzene, 1,4-dinitrobenzene, benzyl chloride, benzyl bromide, trifluoromethoxybenzene, and trifluoroethoxybenzene.

21. The method of claim 8, wherein when $R_3$ is substituted phenyl the substituted phenyl is selected from the group consisting of chlorobenzene, bromobenzene, fluorobenzene, 1,2-dichlorobenzene, 1,2-dibromobenzene, 1,2-difluorobenzene, 1,3-dichlorobenzene, 1,3-dibromobenzene, 1,3-difluorobenzene, 1,4-difluorobenzene, 1,4-dibromobenzene, 1,4-difluorobenzene, methylbenzene, ethylbenzene, o-xylene, m-xylene, p-xylene, 2-ethyl toluene, 3-ethyl toluene, 4-ethyl toluene, propyl benzene, cumene, butyl benzene, sec-butyl benzene, iso-butyl benzene, tert-butyl benzene, o-cymene, m-cymene, p-cymene, 1,2-diethyl benzene, 1,3-diethyl benzene, 1,4-diethylbenzene, 1,3-di-tert-butyl benzene, 1,4-di-tert-butyl benzene, 4-tert butyl toluene, anisole, 2-methyl anisole, 3-methyl anisole, 4-methyl anisole, 1,2-benzenedimethanol, 1,3-benzenedimethanol, 1,4-benzenedimethanol, 1,2-dimethoxybenzene, 2-ethoxyanisole, 3,5-diethoxytoluene, benzylmercaptan, phenethylmercaptan, 1,2-benzenedimethanethiol, 1,3-benzenedimethanethiol, 1,4-benzenedimethanethiol, nitrobenzene, 1,2-dinitrobenzene, 1,3-dinitrobenzene, 1,4-dinitrobenzene, benzyl chloride, benzyl bromide, trifluoromethoxybenzene, and trifluoroethoxybenzene.

22. The process of claim 10, wherein when $R_3$ is substituted phenyl the substituted phenyl is selected from the group consisting of chlorobenzene, bromobenzene, fluorobenzene, 1,2-dichlorobenzene, 1,2-dibromobenzene, 1,2-difluorobenzene, 1,3-dichlorobenzene, 1,3-dibromobenzene, 1,3-difluorobenzene, 1,4-difluorobenzene, 1,4-dibromobenzene, 1,4-difluorobenzene, methylbenzene, ethylbenzene, o-xylene, m-xylene, p-xylene, 2-ethyl toluene, 3-ethyl toluene, 4-ethyl toluene, propyl benzene, cumene, butyl benzene, sec-butyl benzene, iso-butyl benzene, tert-butyl benzene, o-cymene, m-cymene, p-cymene, 1,2-diethyl benzene, 1,3-diethyl benzene, 1,4-diethylbenzene, 1,3-di-tert-butyl benzene, 1,4-di-tert-butyl benzene, 4-tert butyl toluene, anisole, 2-methyl anisole, 3-methyl anisole, 4-methyl anisole, 1,2-benzenedimethanol, 1,3-benzenedimethanol, 1,4-benzenedimethanol, 1,2-dimethoxybenzene, 2-ethoxyanisole, 3,5-diethoxytoluene, benzylmercaptan, phenethylmercaptan, 1,2-benzenedimethanethiol, 1,3-benzenedimethanethiol, 1,4-benzenedimethanethiol, nitrobenzene, 1,2-dinitrobenzene, 1,3-dinitrobenzene, 1,4-dinitrobenzene, benzyl chloride, benzyl bromide, trifluoromethoxybenzene, and trifluoroethoxybenzene.

* * * * *